United States Patent [19]

Hargrave et al.

[11] Patent Number: 5,366,972
[45] Date of Patent: Nov. 22, 1994

[54] 5,11-DIHYDRO-6H-DIPYRIDO(3,2-B:2',3'-E)(1,4)DIAZEPINES AND THEIR USE IN THE PREVENTION OR TREATMENT OF HIV INFECTION

[75] Inventors: Karl D. Hargrave, Brookfield; John R. Proudfoot, Newtown; Julian Adams; Karl G. Grozinger, both of Ridgefield, all of Conn.; Gunther Schmidt, deceased, late of Munich, Germany, by Margaret Schmidt, legal representative; Wolfhard Engel, Biberach, Germany; Gunther Trummlitz, Warthausen, Germany; Wolfgang Eberlein, Biberach, Germany

[73] Assignee: Boehringer Ingelheim Pharmaceuticals, Inc., Ridgefield, Conn.

[21] Appl. No.: 91,418

[22] Filed: Jul. 13, 1993

Related U.S. Application Data

[63] Continuation of Ser. No. 740,828, Aug. 5, 1991, abandoned, which is a continuation-in-part of Ser. No. 600,390, Oct. 19, 1990, abandoned, which is a continuation-in-part of Ser. No. 579,001, Sep. 6, 1990, abandoned, which is a continuation-in-part of Ser. No. 438,923, Nov. 17, 1989, abandoned, which is a continuation-in-part of Ser. No. 372,974, Jun. 28, 1989, abandoned, which is a continuation-in-part of Ser. No. 340,970, Apr. 20, 1989, abandoned.

[51] Int. Cl.$^5$ ............... A61K 31/55; C07D 471/14
[52] U.S. Cl. ..................... 514/220; 514/311; 540/495; 540/557; 540/560
[58] Field of Search ........... 540/495, 557, 560; 514/220, 311

[56] References Cited

U.S. PATENT DOCUMENTS

| 4,659,707 | 4/1987 | Giano et al. | 540/495 |
| 4,873,236 | 10/1989 | Engel et al. | 540/495 |

FOREIGN PATENT DOCUMENTS

| 835391 | 2/1970 | Canada | 540/495 |
| 0066774 | 12/1982 | European Pat. Off. | 540/495 |
| 0312895 | 4/1989 | European Pat. Off. | 540/495 |
| A0393529 | 10/1990 | European Pat. Off. | 540/495 |
| 0393604 | 10/1990 | European Pat. Off. | 540/495 |
| A0410148 | 1/1991 | European Pat. Off. | 540/495 |
| A0429987 | 6/1991 | European Pat. Off. | 540/495 |
| 1542160 | 10/1968 | France | 540/495 |
| 1916011 | 3/1970 | Germany | 540/495 |
| 1936670 | 2/1971 | Germany | 540/495 |
| 1620572 | 10/1971 | Germany | 540/495 |
| 3643666 | 6/1988 | Germany | 540/495 |

OTHER PUBLICATIONS

Nature, vol. 343, 470–473, Rudi Pauwels, et al.
Chemical Abstracts, vol. 90, No. 17, Apr. 23, 1979, Thomae, Dr. Karl, GmbH, "11-Substituted 5,11-dihydro-6H-pyrido-[2,3-b][1,4]benzodiazepine-6-ones.", page 522, col. 1, abstract No. 90:137875s.
Chemical Abstracts, vol. 90, No. 19, May 7, 1979, Brewster, Keith et al., "The Synthesis of some pyrido[1,4]benzoxazepines and a dipyrido[1,4]oxazepine.", page 611, col. 2, abstract No. 90:152145x.
Chemical Abstracts, vol. 71, No. 23, Dec. 8, 1969, Schmidt, Guenther et al., "Analgesic 5,11-dihydro-6-H-pyrido[2,3-b][1,4]benzodiazepin-6-ones.", p. 394, col. 1, abstract No. 112994z.
Hargrave, Karl D. et al., "Novel Non-Nucleoside Inhibitors of HIV-1 Reverse Transcriptase. 1. Tricyclic Pyridobenzo- and Dipyridodiazepines", *J. Med. Chem.* 1991, 34, 2231–2241.
Merluzzi, Vincent J. et al., "Inhibition of HIV-1 Replication by a Nonnucleoside Reverse Transcriptase Inhibitor", *Science*, 1990, 250, 1411–1413.
Koup, Richard A. et al., "Inhibition of Human Immunodeficiency Virus Type 1 (HIV-1) Replication by the Dipyridodiazepinone BI-RG-587", *The Journal of Infectious Diseases*, 1991, 163, 966–970.
Wu, Joe C. et al., "A Novel Dipyridodiazepinone Inhibitor of HIV-1 Reverse Transcriptase Acts through a Nonsubstrate Binding Site", *Biochemistry*, 1991, 30, 2022–2026.

*Primary Examiner*—Robert T. Bond
*Attorney, Agent, or Firm*—David E. Frankhouser; Alan R. Stempel; Mary-Ellen M. Timbers

[57] ABSTRACT

Disclosed are novel 5,11-dihydro-6H-dipyrido[3,2-b; 2',3'-e][1,4]diazepines. These are useful in the prevention or treatment of HIV infection.

3 Claims, No Drawings

5,11-DIHYDRO-6H-DIPYRIDO(3,2-B:2',3'-E)(1,4)DIAZEPINES AND THEIR USE IN THE PREVENTION OR TREATMENT OF HIV INFECTION

RELATED APPLICATIONS

This is a continuation of application Ser. No. 740,828, filed Aug. 5, 1991 now abandoned, which is in turn a continuation-in-part of application Ser. No. 600,390, filed Oct. 19, 1990. which is in turn a continuation-in-part of application Ser. No. 579,001, filed Sep. 6, 1990, which is in turn a continuation-in-part of application Ser. No. 438,923, filed Nov. 17, 1989, now abandoned, which is in turn a continuation-in-part of application Ser. No. 372,974, filed Jun. 28, 1989, now abandoned, which is in turn a continuation-in-part of application Ser. No. 340,970, filed Apr. 20, 1989, all now abandoned.

FIELD OF THE INVENTION

The invention relates to novel 5,11-dihydro-6H-dipyrido[3,2-b:2',3'-e][1,4]diazepines and pharmaceutically acceptable salts thereof, methods for preparing these compounds, the use of these compounds in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the vital RNA must first be converted into DNA, and then integrated into the host cell's genome, in order for the host cell to produce the required viral proteins. The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Next, acting as a ribonuclease, RT frees the DNA just produced from the original viral RNA and then destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

SUMMARY OF THE INVENTION

A first aspect of the invention comprises novel dipyridodiazepines. These possess inhibitory activity against HIV-1 RT. A second aspect of the invention comprises methods for making these novel compounds. A third aspect of the invention is a method for preventing or treating HIV-1 infection which comprises administering, to a human being exposed to or infected by HIV-1, a prophylactically or therapeutically effective amount of one of the above-mentioned novel compounds. A final aspect of the invention comprises pharmaceutical compositions suitable for the prevention or treatment of HIV-1 infection comprising the above-mentioned compounds.

DESCRIPTION OF THE INVENTION

In one of its composition of matter aspects, the invention comprises 5,11-dihydro-6H-dipyrido[3,2-b:2',3'-e][1,4]diazepines of the formula I

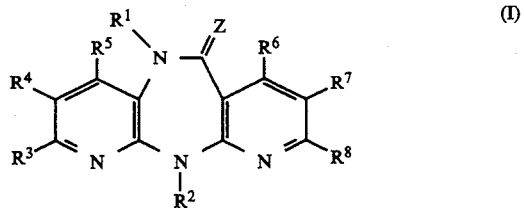

wherein,

Z is oxygen, sulfur, $=NCN$ or a group of the formula $=NOR^9$ wherein $R^9$ is alkyl of 1 to 3 carbon atoms;

$R^1$ is hydrogen, alkyl of 1 to 6 carbon atoms, fluoroalkyl of 1 to 6 carbon atoms and 1 to 3 fluorine atoms, cycloalkyl of 3 to 6 carbon atoms, alkenylmethyl or alkynylmethyl of 3 to 6 carbon atoms, 2-halo-2-propen-1-yl, mono- or di-halovinyl, aryl or arylmethyl (wherein the aryl moiety is phenyl, thienyl or furanyl, which is either unsubstituted or substituted by methyl, methoxy or halogen), alkanoyl or thioalkanoyl of 2 to 4 carbon atoms, alkylsulfonyl of 1 to 4 carbon atoms, aminocarbonyl, mono- or di-alkylaminocarbonyl wherein each alkyl moiety contains 1 to 2 carbon atoms, aminoethyl, mono- or di-alkylaminoethyl wherein each alkyl moiety contains 1 to 2 carbon atoms, alkyloxyalkyl or alkylthioalkyl of 2 to 4 carbon atoms, alkyloxycarbonyl wherein the alkyl moiety contains 1 to 4 carbon atoms, alkenyloxycarbonyl wherein the alkenyl moiety contains 2 to 4 carbon atoms, hydroxy, alkyloxy of 1 to 4 carbon atoms, cyano, amino, mono- or di-alkylamino wherein each alkyl moiety contains 1 to 4 carbon atoms, aminocarbonylmethyl, mono- or di-alkylaminocarbonylmethyl wherein the alkyl moiety contains 1 to 2 carbon atoms, or cyanoalkyl wherein the alkyl moiety contains 1 to 4 carbon atoms;

$R^2$ is hydrogen (with the proviso that $R^1$ is not hydrogen), alkyl of 1 to 6 carbon atoms, fluoroalkyl of 1 to 6 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 6 carbon atoms, alkyloxyalkyl or alkylthioalkyl of 2 to 5 carbon atoms, alkanoyl or thioalkanoyl of 2 to 5 carbon atoms, cyano, cyanoalkyl of 2 to 5 carbon atoms, hydroxyalkyl or acyloxyalkyl wherein the alkyl moiety contains 2 to 6 carbon atoms and the acyl moiety contains 2 to 3 carbon atoms, oxazolyl, isoxazolyl, thiazolyl, aryl or arylmethyl (wherein the aryl moiety is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 5 carbon atoms;

one of $R^3$, $R^4$ and $R^5$ is alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxyalkyl or alkylthioalkyl of 2 to 5 carbon atoms, alkyloxycarbonylalkyl wherein the alkyl moieties each contain 1 to 2 carbon atoms, carboxyalkyl or cyanoalkyl wherein the alkyl moieties each contain 1 to 5 carbon atoms, mono- or di-alkylaminocarbonylalkyl wherein the alkyl moieties each contain 1 to 2 carbon atoms, hydroxyl, mercapto, alkyloxy or alkylthio of 1 to 5 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkyloxycarbonyl wherein the alkyl moiety contains 1 to 3 carbon atoms. mono- or di-alkylaminocarbonyl wherein each alkyl moiety contains 1 to 3 carbon atoms, aminoalkyl of 1 to 4 carbon atoms, mono- or di-alkylaminoalkyl wherein each alkyl moiety contains 1 to 3 carbon atoms, imidazol-2-yl, imidazol-4-yl, aryl or arylalkyl (wherein the aryl moiety is phenyl, thienyl, furanyl, or pyridyl, which is either unsubstituted or substituted by alkyl or alkyloxy of 1 to 3 carbon atoms, hydroxyl, amino, or halogen, and the alkyl moiety contains 1 to 3 carbon atoms which may be unsubstituted or substituted with a methyl, hydroxyl, or amino groups), a group of the formula —$NR^{10}R^{11}$, halogen, cyano, nitro, azido or carboxyl, with the other two substituents being hydrogen, methyl or halogen; or, two of $R^3$, $R^4$ and $R^5$ are independently alkyl of 2 to 3 carbon atoms, hydroxyalkyl of 1 to 3 carbon atoms, trihalomethyl, alkyloxy or alkylthio of 1 to 2 carbon atoms, or a group of the formula —$NR^{10}R^{11}$, with the remaining substituent being hydrogen, methyl, or halogen; or, two of $R^3$ and $R^4$ or $R^4$ and $R^5$ are joined to form a cycloalkyl with a 3 or 4 carbon bridge, or a fused pyridine ring; or, $R^3$, $R^4$ and $R^5$ are each hydrogen;

one of $R^6$, $R^7$ and $R^8$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 4 carbon atoms, hydroxyalkyloxy of 2 to 4 carbon atoms, alkanoyloxy of 2 to 4 carbon atoms, alkylsulfinyl or alkylsulfonyl of 1 to 4 carbon atoms, alkanoyl of 2 to 6 carbon atoms, alkoxycarbonyl wherein the alkyl moiety contains 1 to 3 carbon atoms, aminoalkyl of 1 to 4 carbon atoms, mono- or di-alkylaminoalkyl wherein each alkyl moiety contains 1 to 2 carbon atoms, a group of the formula —$NR^{12}R^{13}$, halogen, cyano, nitro, azido or carboxyl, with the other two substituents being hydrogen; or, two of $R^6$, $R^7$ and $R^8$ are independently alkyl of 1 to 2 carbon atoms, trihalomethyl, alkyloxy or alkylthio of 1 to 2 carbon atoms, halogen or a group of the formula —$NR^{12}R^{13}$, with the remaining substituent being hydrogen; or, $R^6$, $R^7$ and $R^8$ are each hydrogen; and, $R^{10}$, $R^{11}$, $R^{12}$ and $R^{13}$ are each independently hydrogen, alkyl of 1 to 4 carbon atoms, alkenylmethyl or alkynylmethyl of 3 to 4 carbon atoms, aryl or arylalkyl (wherein the aryl moiety is phenyl, thienyl, furanyl, or pyridyl which is either unsubstituted or substituted by methyl, methoxy, hydroxyl, or halogen, and the alkyl moiety contains 1 to 3 carbon atoms). mono- or dihydroxy(or acetoxy)alkylmethyl wherein the alkyl moiety contains 1 to 3 carbon atoms, alkyloxyethyl or alkylthioethyl of 3 to 4 carbon atoms, aminoalkylmethyl of 2 to 4 carbon atoms, mono- or di-alkylaminoalkylmethyl wherein each alkyl moiety contains 1 or 2 carbon atoms, or alkanoyl of 1 to 4 carbon atoms; or, $R^{10}$ and $R^{11}$, and $R^{12}$ and $R^{13}$, together with the nitrogen atoms between them, respectively and independently form azetidin-1-yl or a 5, 6 or 7-membered ring which is either saturated or unsaturated, which optionally contains up to one additional heteroatom which may be selected from O, S or N, or which optionally contains in place of a carbon atom a carbonyl moiety or a group of the formula —$N(R^{14})$— wherein $R^{14}$ is hydrogen or alkyl of 1 to 2 carbon atoms, and which ring is optionally and, independently substituted with hydroxymethyl, aminomethyl, 1 to 4 methyl groups and 1 to 2 hydroxy groups.

A subgeneric aspect of the invention comprises compounds of formula I, wherein,

Z is oxygen, sulfur or a group of the formula =$NOR^9$ wherein $R^9$ is alkyl of 1 to 2 carbon atoms;

$R^1$ is hydrogen, alkyl of 1 to 4 carbon atoms, fluoroalkyl of 1 to 4 carbon atoms, cyclopropyl, alkenylmethyl or alkynylmethyl of 3 to 4 carbon atoms, 2-halo-2-propen-1-yl, alkanoyl of 2 to 3 carbon atoms, alkyloxyalkyl or alkylthioalkyl of 2 to 3 carbon atoms, or cyanoalkyl wherein the alkyl moiety contains 1 to 3 carbon atoms;

$R^2$ is hydrogen (with the proviso that $R^1$ is not hydrogen), alkyl of 1 to 5 carbon atoms, fluoroalkyl of 1 to 5 carbon atoms, cycloalkyl of 3 to 5 carbon atoms, oxetanyl, thietanyl, alkenylmethyl or alkynylmethyl of 3 to 5 carbon atoms, alkyloxyalkyl or alkylthioalkyl of 2 to 4 carbon atoms, alkanoyl of 2 to 4 carbon atoms, hydroxyalkyl of 2 to 5 carbon atoms, aryl or arylmethyl (wherein the aryl moiety is phenyl, thienyl or furanyl, which is either unsubstituted or substituted by alkyl or alkyloxy of 1 to 3 carbon atoms, hydroxyl or halogen), or alkyloxycarbonylmethyl wherein the alkyl moiety contains 1 to 4 carbon atoms;

one of $R^3$, $R^4$ and $R^5$ is alkyl of 1 to 4 carbon atoms, alkenyl or alkynyl of 2 to 4 carbon atoms, trihalomethyl, hydroxyalkyl of 1 to 4 carbon atoms, alkyloxyalkyl or alkylthioalkyl of 2 to 4 carbon atoms, alkyloxycarbonylalkyl wherein the alkyl moieties each contain 1 to 2 carbon atoms, hydroxyl, alkyloxy or alkylthio of 1 to 3 carbon atoms, hydroxyalkyloxy of 2 to 3 carbon atoms, alkanoyloxy of 2 to 3 carbon atoms, alkylsulfinyl or alkylsulfonyl of 1 to 3 carbon atoms, alkanoyl of 2 to 4 carbon atoms, alkyloxycarbonyl wherein the alkyl moiety contains 1 to 2 carbon atoms, aminoalkyl of 1 to 3 carbon atoms, mono- or dialkylaminoalkyl wherein each alkyl moiety contains 1 to 2 carbon atoms, amino, mono- or dialkylamino wherein each alkyl moiety contains 1 to 4 carbon atoms, azetidin-1-yl, pyrrol-1-yl, pyrrolin-1-yl, pyrrolidin-1-yl, pyrazolo-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, 4-methyl)piperazin-1-yl, piperazin-1-yl, (2-hydroxy(or acetoxy)ethyl)amino, N-methyl-N-(2-hydroxy(or acetoxy)ethyl)amino, N-methyl-N-(2-methoxyethyl)amino, or halogen, with the other two substituents being hydrogen, methyl or chloro; or, two of $R^3$, $R^4$ and $R^5$ are independently alkyl of 1 to 2 carbon atoms, alkyloxy or alkylthio of 1 to 2 carbon atoms, amino, mono- or di-alkylamino wherein each alkyl moiety contains 1 to 3 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, (2-hydroxy(or acetoxy)ethyl)amino, N-methyl-N-(2-hydroxy(or acetoxy)ethyl)amino, N-methyl-N-(2-methoxyethyl)amino, with the remaining substituent being hydrogen, methyl or chloro; or, $R^3$, $R^4$ and $R^5$ are each hydrogen;

one of $R^6$, $R^7$ and $R^8$ is alkyl of 1 to 2 carbon atoms, vinyl, trifluoromethyl, hydroxyalkyl of 1 to 2 carbon atoms, hydroxyl, alkyloxy or alkylthio of 1 to 2 carbon atoms, hydroxyalkyloxy of 2 to 3 carbon atoms, alkanoyloxy of 2 to 3 carbon atoms, amino, mono- or di-alkylamino wherein each alkyl moiety contains 1 to 2 carbon atoms, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, (2-hydroxy-(or acetoxy)ethyl)amino, N-methyl-N-(2-hydroxy-(or acetoxy)ethyl)amino, N-methyl-N-(2-methoxyethyl)amino, or halogen, with the other two substituents being hydrogen; or, $R^6$, $R^7$ and $R^8$ are each hydrogen.

A particular subgeneric aspect of the invention comprises compounds of formula I wherein, Z is oxygen or sulfur;

$R^1$ is hydrogen, alkyl of 1 to 3 carbon atoms or allyl;

$R^2$ is alkyl of 2 to 3 carbon atoms, or cycloalkyl of 3 to 4 carbon atoms;

$R^3$ is hydrogen, methyl, alkyloxy or alkylthio of 1 to 3 carbon atoms, chloro, amino, mono- or di-alkylamino wherein each alkyl moiety contains 1 to 3 carbon atoms, allylamino, azetidin-1-yl, pyrrol-1-yl, pyrrolin-1-yl, pyrrolidin-1-yl, pyrazol-1-yl, pyrazolin-1-yl, pyrazolidin-1-yl, imidazol-1-yl, imidazolin-1-yl, imidazolidin-1-yl, tetrahydropyridin-1-yl, piperidin-1-yl, morpholin-1-yl, (4-methyl)piperazin-1-yl, piperazin-1-yl, or N-methyl-N-(2-hydroxy(or acetoxy)ethyl)amino;

$R^4$ is hydrogen, methyl or chloro;

$R^5$ is hydrogen, methyl, ethyl, chloro, or trifluoromethyl;

$R^6$ and $R^8$ are hydrogen; and $R^7$ is hydrogen or amino.

A more particular subgeneric aspect of the invention comprises compounds of formula I wherein, Z is oxygen or sulfur;

$R^1$ is hydrogen, alkyl of 1 to 3 carbon atoms or allyl;

$R^2$ is alkyl of 2 to 3 carbon atoms, or cycloalkyl of 3 to 4 carbon atoms;

$R^3$ is hydrogen, methyl, chloro, methoxy, ethoxy, amino, mono- or di-alkylamino wherein each alkyl moiety contains 1 to 2 carbon atoms, allylamino, allylmethylamino, pyrrolin-1-yl, pyrrolidin-1-yl, tetrahydropyridin-1-yl, piperidin-1-yl or morpholin-1-yl;

$R^4$ is hydrogen;

$R^5$ is hydrogen, methyl, ethyl, chloro, or trifluoromethyl;

$R^6$ and $R^8$ are hydrogen; and $R^7$ is hydrogen or amino.

Preferred compounds of formula I are:
5,11-dihydro-11-ethyl-4-methyl-6H-dipyrido[3,2-b:2',3'-e][1,4]diazepin-6-one or -thione; 11-cyclopropyl-5,11-dihydro-4-methyl-6H-dipyrido[3,2-b:2',3'-e][1,4]diazepin-6-one or -thione;
5,11-dihydro-11-ethyl-2,4-dimethyl-6H-dipyrido[3,2-b:2',3'-e][1,4]diazepin-6-one or -thione; 11-cyclopropyl-5,11-dihydro-2,4-dimethyl-6H-dipyrido[3,2-b:2',3'-e][1,4]diazepin-6-one or -thione;
2-chloro-5,11-dihydro-11-ethyl-4-methyl-6H-dipyrido[3,2-b:2',3'-e][1,4]diazepin-6-one or -thione;
2-chloro-11-cyclopropyl-5,11-dihydro-4-methyl-6H-dipyrido[3,2-b:2',3'-e][1,4]diazepin-6-one or -thione;
5,11-dihydro-11-ethyl-2-methoxy-4-methyl-6H-dipyrido[3,2-b:2',3'-e][1,4]diazepin-6-one or -thione;
11-cyclopropyl-5,11-dihydro-2-methoxy-4-methyl-6H-dipyrido[3,2-b:2',3'-e][1,4]diazepin-6-one or -thione;
3,4-dimethyl-5,11-dihydro-11-ethyl-6H-dipyrido[3,2-b:2',3'-e][1,4]diazepin-6-one or -thione; 2-chloro-5,11-dihydro-11-ethyl-5-methyl-6H-dipyrido[3,2-b:2',3'-e][1,4]diapezin-6-one or-thione;
2-bromo-5,11-dihydro-11-ethyl-4-methyl-6H-dipyrido[3,2-b:2',3'-e][1,4]diazepin-6-one or -thione;
5,11-dihydro-11-ethyl-4-methyl-2-(N,N-dimethylamino)-6H-dipyrido[3,2-b:2',3'-e][1,4]diazepin-6-one or -thione; and,
11-cyclopropyl-5,11-dihydro-4-methyl-2-(N,N-dimethylamino)-6H-dipyrido[3,2-b:2',3'-e][1,4]diazepin-6-one or -thione.

Synthesis Of Compounds Of Formula I And Their Salts

The compounds of Formula I and their salts can be prepared by known methods or obvious modifications thereof. Methods A–H, described below, are illustrative of the methods for preparing the compounds.

Method A

Compounds of the formula Ia

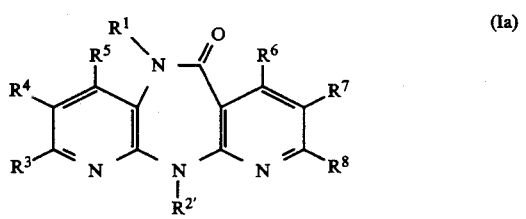

wherein $R^1$ and $R^3$ through $R^8$ are defined as above and $R^{2'}$ has the same definitions as $R^2$ with the exception of hydrogen, can be obtained by cyclizing carboxylic acid amides of formula II,

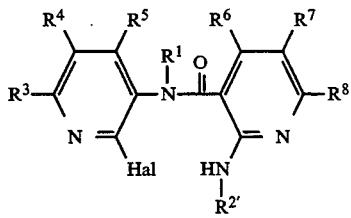

(II)

wherein $R^1$, $R^3$ through $R^8$ and $R^{2'}$ have the same definitions set forth with respect to Formula Ia and Hal represents fluorine, chlorine, bromine or iodine.

A variant of this method, which is preferably used to prepare compounds of formula Ia wherein $R^6$, $R^7$, or $R^8$, especially $R^7$, are electron withdrawing groups, such as nitro, involves cyclizing carboxylic acid amides of formula IIa,

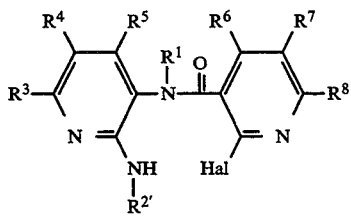

(IIa)

wherein $R^3$ through $R^8$ are defined as above and $R^{2'}$ has the same definitions as $R^2$ with the exception of hydrogen, and Hal represents fluorine, chlorine, bromine or iodine.

Cyclization is conveniently carried out by the conversion of compounds of formula II or IIa into their alkaline metal salts and subsequent condensation at temperatures between 0° C. and the boiling point of the reaction mixture. If, in the starting compounds of formula II or IIa, $R^1$ is different from hydrogen, metallation requires at least 1 mole of the metallating agent. If, on the other hand, $R^1$ is hydrogen, at least 2 moles of this agent must be used. For metallation, lithium, sodium and potassium hydrides or lithium alkyls, such as n-butyl lithium, are preferably used.

The cyclization reaction is usually carried out in inert solvents, e.g. in tetrahydrofuran, 1,4-dioxane, glycoldimethyl ether, diethylene-glycoldimethyl ether, triethyleneglycoldimethyl ether, dimethylformamide, pyridine, xylene, benzene or anisole. Cyclization may also be effected by heating carboxylic acid amides of formula II or IIa in dipolar aprotic solvents, preferably in sulfolane or dimethylsulfone. Catalytic quantities of strong acids, e.g. sulfuric acid, hydrochloric acid, hydrobromic acid, phosphoric acid, polyphosphoric acid, methanesulfonic acid or p-toluenesulfonic acid, have proved to be of use. The necessary reaction temperature is usually between 110° and 220° C.

Method B

Compounds of formula Ib

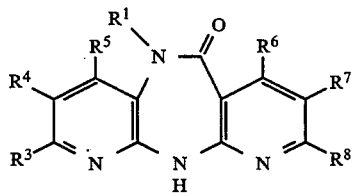

(Ib)

wherein $R^1$ and $R^3$ through $R^8$ are defined as above, can be prepared by hydrolytic cleavage of the arylmethyl group in compounds of formula III,

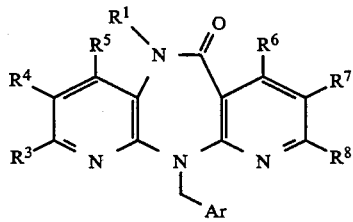

(III)

wherein $R^1$ and $R^3$ through $R^8$ are defined as mentioned above and Ar can be, for example, a phenyl or 4-methoxyphenyl group. Hydrolysis is effected by moderate to strong acids or Lewis-acids at temperatures between −20° and +150° C. Such acids can be, for example, sulfuric acid, methanesulfonic acid, trifluoroacetic acid, trifluoromethanesulfonic acid, phosphoric or polyphosphoric acid. When using phosphoric or polyphosphoric acid, the addition of solvents such as benzene, toluene, phenol, anisole or veratrole has proved to be of advantage.

If Lewis acids, such as aluminum chloride or bromide are used to eliminate the arylmethyl group, solvents such as aromatic hydrocarbons, e.g. benzene, toluene, anisole, or mixtures thereof with dichloromethane are suitable.

It will be obvious to those skilled in the art that Method B is not preferred in those cases wherein any of $R^1$ and $R^3$ through $R^8$ are readily hydrolyzable substituents, for example, wherein $R^1$ is alkanoyl or any of $R^3$ through $R^8$ are alkanoylamino or alkoxycarbonyl. In cases wherein $R^1$ is alkanoyl or any of $R^3$ through $R^8$ are alkoxycarbonyl, for example, it is preferable to utilize method A described above; when $R^1$ is hydrogen two equivalents of base must be used. In cases wherein any of $R^3$ through $R^8$ are alkanoylamino, for example, it is preferable to carry out the hydrolysis (and subsequent acylation) on the corresponding nitro derivative, and then reduce the nitro moiety to the amine, followed by acylation to yield the desired product.

Method C

A compound of formula Ic

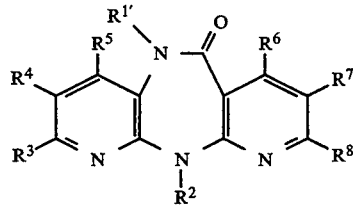

(Ic)

wherein $R^{1'}$ has the same definitions as $R^1$ with the exception of hydrogen and $R^2$ through $R^8$ are defined as above, may be obtained by converting a 5,11-dihydro-6H-dipyrido[3,2-b:2′,3′-e][1,4]diazepin-6-one of the formula IV

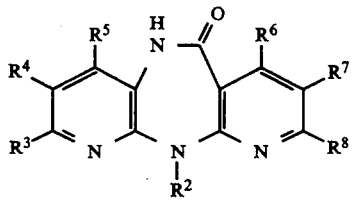 (IV)

wherein $R^2$ through $R^8$ are defined as above, into the corresponding 5-alkali or alkaline earth metal compound and subsequently reacting the alkali metal compound with a compound of the formula V $R^{1'}X$ (V)

wherein $R^{1'}$ has the same meanings as in formula Ic and X is the radical of a reactive ester, a halogen atom, the group $OSO_2OR^{1'}$, the methanesulfonyloxy or ethanesulfonyloxy group or an aromatic sulfonyloxy group. Instead of converting the compound of the formula IV into its corresponding alkali metal salt in the first step, the alkylation of a compound of formula IV may also be performed by reaction with a compound of formula V in the presence of amines, such as triethylamine, diazabicycloundecene or 4-(dimethylamino)pyridine, or of alkali carbonates or bicarbonates, such as sodium and potassium carbonate or sodium bicarbonate.

The conversion of a compound of formula IV into the corresponding alkali metal or alkaline earth metal compound may be effected by reacting a compound of formula IV with an alkali metal or alkaline earth metal hydroxide, such as lithium hydroxide, barium hydroxide, sodium hydroxide or potassium hydroxide, with an alkali metal alkoxide, such as sodium methoxide or potassium tert-butoxide, with an alkali metal amide, such as sodium amide or potassium amide, or with an alkali metal hydride such as sodium hydride or potassium hydride. The reaction is generally carried out in the presence of a suitable organic solvent at temperatures between $-78°$ C. and $+60°$ C., preferably at room temperature. Inert organic solvents, such as dimethylformamide, dimethylsulfoxide, tetrahydrofuran, glycoldimethyl ether, toluene, or pyridine are preferred if alkali metal hydrides are used as the metallating agents, whereas, if an alkali or alkaline earth metal hydroxide is used, an aqueous mixture with an organic solvent, such as methanol or tetrahydrofuran, may also be employed. For conversion of the alkali or alkaline earth metal-substituted 5,11-dihydro-6H-dipyrido[3,2-b:2′,3′-e][1,4]diazepin-6-one thus obtained into a compound of general formula Ic, the solution or suspension of the alkali or alkaline earth metal compound is reacted directly, i.e. without isolation, with a compound of formula V at $-20°$ C. or at elevated temperatures, up to the boiling point of the solvent or reaction medium, whichever is lower. The substitution takes place almost exclusively at the nitrogen atom in the 5-position of the dihydro-dipyridodiazepinone, even if $R^2$ in the starting material of formula IV is a hydrogen atom, provided that one equivalent of base and one equivalent of a compound of formula V are used.

It will be obvious to those skilled in the art that the presence of nucleophilic substituents in the compounds of formula Ic may require the use of an intermediate of formula Ic having substituents which are, other than the 11-position nitrogen, not nucleophilic but which can be derivatized to yield the required group. For example, amino or monoalkylamino substituents at any of $R^3$ through $R^8$ are preferably obtained by alkylating or acylating an intermediate of formula Ic having a nitro group at any of $R^3$ through $R^8$, and subsequently reducing the nitro group, and alkylating, if appropriate, to yield the final product.

Method D

A compound of formula I

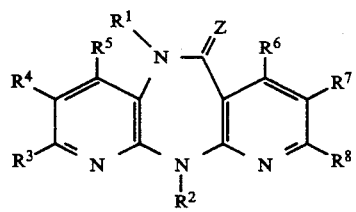 (I)

wherein Z is oxygen and $R^1$ through $R^8$ represent the groups mentioned above, can be obtained by converting a 5,11-dihydro-6H-dipyrido[3,2-b:2′,3′-e][1,4]diazepin-6-one of formula Ib, as described above, into the corresponding metal salt of formula VIa or—in the case of $R^1$ in the compound of formula Ib being hydrogen—into a compound of formula VIb

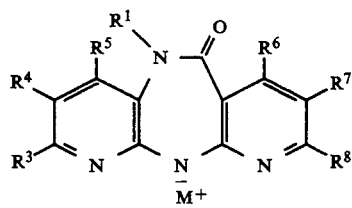 (VIa)

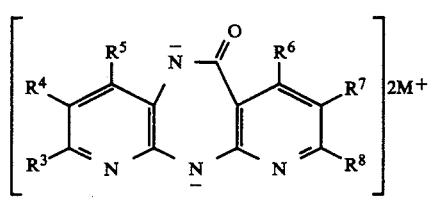 (VIb)

wherein M represents an alkali metal, such as lithium, sodium, potassium, rubidium or cesium, or M represents the group MgHal+, wherein Hal is a chlorine, bromine or iodine atom, and subsequently alkylating with a compound of formula VII $R^2X$ (VII)

wherein $R^2$ and X are as hereinbefore defined.

The conversion of a compound of formula Ib into the corresponding alkali metal compound of formulae VIa or VIb may be effected by reacting a compound of formula Ib with a lithium alkyl (e.g. n-butyl lithium, or t-butyl lithium) optionally in the presence of tetramethylethylenediamine, a lithium dialkylamide, (e.g. lithium diisopropylamide, lithium dicyclohexylamide and lithium isopropyl-cyclohexylamide), a lithium aryl (e.g. phenyl lithium), an alkali metal hydroxide (e.g. lithium, sodium or potassium hydroxide), an alkali metal hydride (e.g. sodium or potassium hydride), an alkali metal amide (e.g. sodium or potassium amides) or a Grignard reagent (e.g. methyl magnesium iodide, ethyl magnesium bromide or phenyl magnesium bromide). One equivalent of base is required for the formation of compounds of formula VIa, whereas two equivalents of base are required for the formation of compounds of formula VIb. The metallation is conveniently carded out in an inert organic solvent at temperatures of between −78° C. and the boiling point of the reaction mixture in question. If a lithium alkyl, lithium aryl, lithium dialkylamide or Grignard reagent is used for the metallation, the preferred solvents are ethers such as tetrahydrofuran, diethyl ether or dioxane, optionally in a mixture with aliphatic or aromatic hydrocarbons, such as hexane or benzene, and the operation may be carried out at temperatures of between −20° and +80° C. When metallation is effected with an alkali metal hydride or alkali metal amide, in addition to the solvents mentioned hereinbefore it is also possible to use xylene, toluene, acetonitrile, dimethylformamide and dimethylsulfoxide, while if an alkali metal hydroxide is used it is also possible to use alcohols such as ethanol, methanol and aliphatic ketones such as acetone, as well as mixtures of these solvents with water.

For conversion of the alkali metal salt thus obtained into a compound of formula I, the solution or suspension of the alkali metal compound is reacted directly, i.e. without isolation of the reaction product, with a compound of formula VII at temperatures of between −20° and the boiling point of the reaction mixture, preferably at room temperature.

It will be obvious to those skilled in the art that the presence of nucleophilic substituents in the compounds of formula I may require the use of an intermediate of formula I having substituents which are, other than the 11-position nitrogen, not nucleophilic but which can be derivatized to yield the required group. For example, amino or monoalkylamino substituents at any of $R^3$ through $R^8$ are preferably obtained by alkylating or acylating an intermediate of formula Ic having a nitro group at any of $R^3$ through $R^8$, and subsequently reducing the nitro group, and alkylating, if appropriate, to yield the final product.

Starting Materials For Methods A–D

The carboxylic acid amides of formula II used as starting materials are obtained, for example, by amination of 2-chloro-nicotinic acid amides of formula VIII

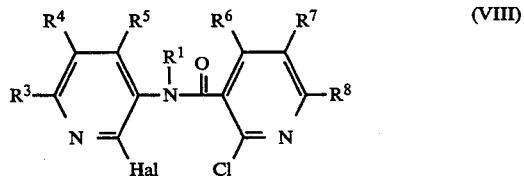

wherein $R^1$ through $R^8$ and Hal are as hereinbefore defined, with primary amines of formula IX

wherein $R^{2'}$ is as hereinbefore defined. The reaction can also be carded out in the presence of inorganic or organic auxiliary bases, such as triethylamine, N,N-dimethylaniline, or sodium or potassium carbonate. The reaction can be carried out without using a solvent; it is of some advantage, however, to use inert organic solvents at temperatures of between 0° C. and 175° C., preferably at reflux temperature. Suitable inert solvents that can be used include an excess of the primary amine of general formula IX, open chain or cyclic ethers, such as tetrahydrofuran, 1,4-dioxane, glycoldimethyl ether, diethyleneglycoldimethyl ether; aromatic hydrocarbons, such as benzene, toluene, xylene, chlorobenzene or pyridine; alcohols such as methanol, ethanol, isopropanol; dipolar aprotic solvents such as dimethylformamide; 1,3-dimethyl-2-imidazolidinone, 1,3-dimethyltetrahydro-2(1H)-pyrimidinone and sulfolane.

Carboxylic acid amides of formula IIa can be prepared by condensation of an appropriately substituted 2-chloronicotinic acid chloride with an appropriately substituted 3-amino-2-(alkylamino)pyridine, under well known reaction conditions.

Starting materials of formula VIII, wherein $R^1$ is different from hydrogen, can be prepared from 2-chloronicotinic acid amides of formula X

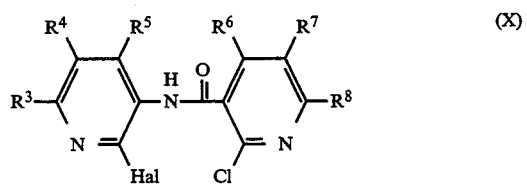

by reaction with alkylating agents of formula V in the presence of proton acceptors, for example of amines, such as triethylamine, diazabicycloundecene, 4-(dimethylamino)pyridine, or alkali or alkaline earth metal hydroxides, such as sodium hydroxide, potassium hydroxide, calcium hydroxide, of alkali carbonates, or alkaline earth metal carbonates or hydrogen carbonates, such as sodium carbonate or potassium carbonate, or potassium hydrogen carbonate.

2-Chloronicotinic acid amides of general formula X can be obtained by condensation of an appropriately substituted 2-chloronicotinic acid chloride with an appropriately substituted 3-amino-2-halopyridine, under well known reaction conditions.

All the other starting materials are known from the literature or may be purchased or may be obtained by procedures known from the literature.

Method E

In Method E, a compound of Formula I, wherein Z is sulfur, is obtained by reacting a compound of Formula I, wherein Z is oxygen, with a sulfurating agent, such as 2,4-bis(4 -methoxyphenyl)-1,3-dithia-2,4-diphosphetane-2,4-disulfide; bis(tricyclohexyltin)sulfide; bis(tri-n-butyltin)sulfide; bis(tri-phenyltin)sulfide; bis(trimethylsilyl)sulfide or phosphorous pentasulfide. The reaction is carried out in an inert organic solvent such as carbon disulfide, benzene or toluene, at room temperature or higher, preferably at an elevated temperature up to the boiling point of the reaction mixture, and preferably under anhydrous conditions. When using the above mentioned tin or silyl sulfides, it is preferable to carry out the sulfurization reaction in the presence of a Lewis acid such as boron trichloride.

It will be obvious to those skilled in the art that the presence of another carbonyl moiety in a compound of formula I, for example, a compound wherein Z is oxygen and any of $R^3$ through $R^8$ is alkanoyl, will require that the ketone carbonyl be protected via known methods by a suitable protecting group prior to the sulfurization reaction; deprotection subsequent to the sulfurization reaction provides the desired compound. Similarly, in cases wherein $R^2$ is, for example, alkanoyl, it will be obvious that the sulfurization reaction is best performed prior to the acylation of the 11-position nitrogen. In those cases wherein the substituents at any of $R^3$ through $R^8$ can be derived from nitro, for example, alkanoylamino, the sulfurization reaction can be performed on the corresponding nitro derivative, followed by an appropriate (known) reduction and finally acylation to yield the desired product.

Method F

Compounds of formula I, wherein $R^1$ is hydrogen and $R^2$ through $R^8$ are as defined above and Z is a group of formula =NCN, can be obtained by reacting a compound of the formula XI

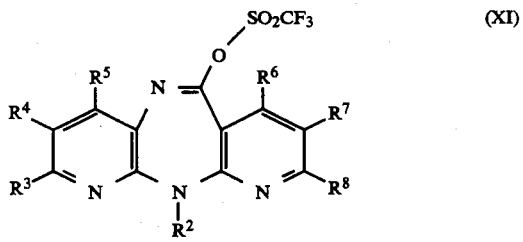

wherein $R^2$ through $R^8$ are as defined above, with cyanamide. The reaction is carried out in the presence of a base such as potassium carbonate, sodium carbonate, triethylamine, or diisopropylethylamine, and in an inert solvent such as methylene chloride, 1,4-dioxane, tetrahydrofuran, diethylether, chloroform, or dimethylformamide at a temperature between 0° C. up to the boiling point of the reaction mixture.

Method G

Compounds of formula I, wherein $R^1$ is hydrogen and $R^2$ through $R^8$ are as defined above and Z is a group of formula =$NOR^9$, can be obtained, in a manner analogous to that of Method F, by reacting a compound of formula XI, wherein $R^2$ through $R^8$ are as defined above with the appropriate alkoxylamine (O-alkylhydroxylamine) or their salts (for example, methoxylamine hydrochloride). The reaction is carried out under conditions analogous to those described for the treatment of compounds of formula XI with cyanamide.

Starting Materials For Methods F and G

Compounds of the formula XI wherein $R^2$ through $R^8$ are as defined above, can be obtained by reacting a compound of formula I, wherein $R^1$ is hydrogen, $R^2$ through $R^8$ are as defined above and Z is oxygen, with trifluoromethanesulfonic anhydride. The reaction is preferably carried out in an inert solvent using one to two equivalents of trifluoromethanesulfonic anhydride and in the presence of one to two equivalents of a base. The base may be, for example, a tertiary amine such as triethylamine or diisopropylethylamine, and the inert solvent used may include, for example, methylene chloride, chloroform, diethylether, tetrahydrofuran, or toluene. Addition of the reagents is generally carried out at or below ambient temperature, and the mixture is then allowed to react, at or near room temperature.

The alkoxylamine starting materials may be purchased or are known from the literature or may be obtained by procedures known from the literature.

Method H

Certain compounds wherein $R^3$ is hydrogen may also be made by the process which is described in copending U.S. patent application Ser. No. 600,451, filed Oct. 19, 1990.

Formation Of Salts And Other Derivatives

Compounds of formula I may, if desired, be converted into their non-toxic, pharmaceutically acceptable salts by conventional methods; for example, by dissolving a compound of formula I in a suitable solvent and treating the solution with one or more molar equivalents of the desired acid or base, as appropriate. The invention also comprises such salts.

Examples of inorganic and organic acids which may form nontoxic, pharmaceutically acceptable acid addition salts with a compound of the formula I are the following: hydrochloric acid, hydrobromic acid, sulfuric acid, phosphoric acid, nitric acid, methanesulfonic acid, tartaric acid, fumaric acid, acetic acid, and the like. Examples of inorganic and organic bases which may form nontoxic, pharmaceutically acceptable basic addition salts with a compound of the formula I are the following: Sodium hydroxide, potassium hydroxide, magnesium hydroxide, ammonia, tromethamine, and the like. Compounds of formula I may form addition salts with one molar equivalent of the acid or base, as appropriate.

Those skilled in the art will realize that it will at times be more convenient to make certain compounds of formula I by derivatization of other compounds of formula I, rather than by making them directly, using one of the above-described Methods A–G. Such derivatizations will employ known reaction techniques. As non-limiting examples, where $R^1$ is hydrogen it can be oxidized to yield hydroxy; a nitro group can be reduced to yield an amine; a methoxy group can converted to hydroxy by standard demethylation procedures and hydroxy can, in appropriate settings, be in turn replaced with amine via the trifluoromethanesulfonyloxy derivative; an amine can be acylated to yield an alkanoylamine or can be alkylated to yield the mono- or dialkylamine; a halogen can be replaced, in appropriate settings, by an amine; and a protecting group can be removed.

Biological Properties

The above described compounds of formula I possess inhibitory activity against HIV-1 reverse transcriptase. When administered in suitable dosage forms, they are useful in the prevention or treatment of AIDS, ARC and related disorders associated with HIV-1 infection. Another aspect of the invention, therefore, is a method for preventing or treating HIV-1 infection which comprises administering to a human being, exposed to or infected by HIV-1, a prophylactically or therapeutically effective amount of a novel compound of Formula I, as described above.

The compounds of formula I may be administered in single or divided doses by the oral, parenteral or topical routes. A suitable oral dosage for a compound of formula I would be in the range of about 0.5 mg to 1 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration.

Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or nonaqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

REVERSE TRANSCRIPTASE (RT) ASSAY

Assay Theory

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate.

Materials a) Preparation of the enzyme

Reverse transcriptase enzyme from the LAV strain of Human Immunodeficiency Virus (HIV-1) (1) was isolated from the bacterial strain JM109 (3) expressing the DNA clone pBRTprt1+ (2) which is under the control of the lac promotor in the expression vector pIBI21 (4). An overnight culture grown in 2XYT medium (37° C., 225 rpm) (5) supplemented with 100 µg/ml ampicillin for positive selection is inoculated at a 1:40 dilution into M9 medium supplemented with 10 µg/ml thiamine, 0.5% casamino acids, and 50 µg/ml ampicillin (5). The culture is incubated (37° C., 225 rpm) until it reaches an OD540 of 0.3-0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/ml) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2X concentrated stock reaction mixture

| Stock Reagent | 2X Mix Concentration |
| --- | --- |
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 µg/ml |
| $^3$H-dGTP (81 µM) | 0.6 µM |

Assay Procedure

The 2X concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 µl/well; 3 wells/compound). The HIV-1 RT enzyme is thawed, diluted in 50 mM Tris pH 7.4 so that fifteen µl of diluted enzyme contain 0.001 Unit (one unit is that amount of enzyme to transform 1 micromole of substrate per minute at 25° C.), and fifteen µl are dispensed per well. Twenty µl of 0.12-0.5M EDTA are added to the first three wells of the microtiter plate. EDTA chelates the $Mg^{++}$ present and prevents reverse transcription. This group serves as background polymerization which is subtracted from all other groups. Twenty-five ul of the 2X reaction mixture are added to all wells and the assay is allowed to incubate at room temperature for 60 minutes. The assay is terminated by precipitating the DNA in each well with 50 µl of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mls of scintillation cocktail and is counted in a Beckman beta counter.

The calculation for percent inhibition is as follows $$\% \text{ inhibition} = \frac{CPM \text{ Mean Test Value} - CPM \text{ Mean Control Value}}{CPM \text{ Mean Control Value}} \times 100$$

References
1. Benn, S., et al., Science 230:949, 1985
2. Farmerie, W. G. et. al., Science 236:305, 1987
3. Yanisch-Perron, C., Viera, J., and Messing, J., Gene 33:103, 1985
4. International Biotechnologies, Inc., New Haven, Conn. 06535
5. Maniatis, T, Fritsch, E. F., and J. Sambrook, eds. *Molecular Cloning: A Laboratory Manual*, Cold Spring Harbor Laboratory, 1982
6. Spira, T., et. al. *J. Clinical Microbiology*, 25:97, 1987.

In order to confirm that compounds which are active in the RT Assay also have the ability to inhibit HIV replication in a living system, compounds according to the invention were also tested in the human T-Cell Culture Assay described below. The results of this testing appear in Table I.

HUMAN T-CELL CULTURE ASSAY

Assay Theory: Formation of syncytia is a feature of in vitro cultures of CD4+ T-cells infected with HIV-1. In this assay, T-cells are treated with a putative replication inhibiting compound and then infected with HIV-1. After incubation, the culture is checked for the formation of syncytia. The absence or reduction in the number of syncytia is used as a measure of the test compound's ability to inhibit HIV replication.

Assay Method: The target cells, designated c8166, are a subclone of human lymphoma cells of T-cell origin and are established at an initial density of $5 \times 10^4$ per 100 ul in RPMI 1640 (+10% fetal bovine serum) culture medium in 96 well flat bottom plates. A selected amount of test compound, dissolved in DMSO, is included. After 24 hours, 50–100 $TCID_{50}$'s (the dose that results in induced effect in 50% of test cultures) of the HTLV-IIIB strain of HIV-1 (2) are inoculated into each culture. Control cultures receive compound or virus only. Four days after virus challenge, cultures are visually examined for the frequency and distribution of virus-induced giant cell syncytia. The percent inhibition by the test compound is determined by comparison with control values. Confirmation of the presence or absence of virus replication is accomplished by harvesting the cell free culture fluids from all experimental groups to determine the presence or absence of infectious progeny through the induction of syncytia formation in secondary human T-cell cultures after 3 days.

References
(1) M. Somasundaran and H. L. Robinson, Science 242, 1554 (1988).
(2) G. M. Shaw, R. H. Hahn, S. K. Arya, J. E. Groopman, R. C. Gallo and F. Wong-Staal, Science 226, 1165 (1984)

In order to assess the specificity of the enzyme inhibitory activity of the compounds provided by the invention, a few were tested, using known per se assay methods, for their ability to inhibit Feline Leukemia Virus-derived reverse transcriptase and Calf Thymus-derived DNA alpha-polymerase. None of the compounds so tested was observed to possess any inhibitory activity against these enzymes. These results indicate that the enzyme inhibitory activity of the compounds provided by the invention is directed rather specifically against HIV-1 RT.

In order to roughly assess the cytotoxicity of the compounds provided by the invention, several such compounds were tested in the MTT Cellular Cytotoxicity Assay described below. The results of this testing are reported in Table I, below. Compounds having a relatively high $EC_{50}$ are preferred.

MTT ASSAY FOR CELLULAR CYTOTOXICITY

Assay Theory

The MTT [3-(4,5-dimethylthiazol-2-yl)-2,5 diphenyl tetrazolium bromide) assay is based on cleavage of tetrazolium bromide by metabolically active cells, resulting in a highly quantitative blue color. This assay has been previously described (1) but has been optimized for the purposes of the testing reported herein.

Assay Method

The H9 cell line (2), an established human lymphoma suspension cell line grown in RPMI 1640 supplemented with 10% fetal bovine serum, is used as the target cell line in the assay. Cells (100 µl) are plated in microtest plate wells at a concentration of $10^5$ cells per ml in the presence of varying concentrations of inhibitor. The cells are incubated at 37° C. in a humidified $CO_2$ incubator. Five days later, 20 µl of MTT (5 mg/ml in RPMI 1640, sonicated, 0.2 micron filtered, and stored at 4° C.) is added to each well. After 4 hours additional incubation at 37° C., 60 µl of Triton-X is added to each well and thoroughly mixed to aid the solubilization of the crystals. Absolute ethanol (5 µl) is added to each well and the resulting mixture is incubated for 30 minutes at 60° C. and immediately read on a plate reacter (Dynatech) at a wavelength of 570 nm.

Data from this assay are used to generate a nonlinear regression analysis which yields an $EC_{50}$.

References
1. Mosmann, Tim, *J. Immunol.* Methods, 65:55, 1983.
2. Jacobs, J. P., *J. Natl. Cancer Inst.*, 34:231, 1965.

| Compound of Example No. | RT Assay % inhibition @ 10 µg/ml | T-Cell Assay % inhibition @ 3 µg/ml | Cytotoxicity Assay ($EC_{50}$, µM) |
|---|---|---|---|
| 2 | 94 | NT | NT |
| 3 | 94 | NT | NT |
| 4 | 98 | 100 | 92 |
| 5 | 44 | NT | NT |
| 6 | 50 | NT | NT |
| 8 | 100 | 100 | 140 |

| Compound of Example No. | RT Assay % inhibition @ 10 μg/ml | T-Cell Assay % inhibition @ 3 μg/ml | Cytotoxicity Assay (EC$_{50}$, μM) | Compound of Example No. | RT Assay % inhibition @ 10 μg/ml | T-Cell Assay % inhibition @ 3 μg/ml | Cytotoxicity Assay (EC$_{50}$, μM) |
|---|---|---|---|---|---|---|---|
| 9 | 100 | 100 | NT | 88 | 0* | NT | NT |
| 10 | 100 | NT | NT | 89 | 38* | NT | NT |
| 11 | 100 | 100 | 200 | 90 | 0* | NT | NT |
| 12 | 100 | 100 | 250 | 91 | 43* | NT | NT |
| 13 | 36* | NT | NT | 92 | 72* | NT | NT |
| 14 | 93† | 100 | 105 | 93 | 90* | NT | NT |
| 15 | 91† | 100 | 45 | 94 | 44 | NT | NT |
| 16 | 96† | 100 | 350 | 95 | 90* | NT | NT |
| 17 | 100 | 100 | NT | 96 | 35* | NT | NT |
| 18 | 100 | NT | NT | 97 | 44 | NT | NT |
| 19 | 81 | NT | NT | 98 | 100 | 100 | NT |
| 20 | 94 | NT | NT | 99 | 77 | NT | NT |
| 21 | 100 | 100 | NT | 100 | 52* | NT | NT |
| 22 | 40* | NT | NT | 101 | 44* | NT | NT |
| 23 | 75* | NT | NT | 102 | 17* | NT | NT |
| 24 | 78* | NT | NT | 103 | 94* | NT | NT |
| 25 | 85* | NT | NT | 104 | 44* | NT | NT |
| 26 | 100 | NT | NT | 105 | 20* | NT | NT |
| 27 | 76* | NT | NT | 106 | 42* | NT | NT |
| 28 | 100 | NT | NT | 107 | 96 | NT | NT |
| 29 | 91* | NT | NT | 108 | 72* | NT | NT |
| 30 | 90* | NT | NT | 109 | 17* | NT | NT |
| 31 | 66 | NT | NT | 110 | 30# | NT | NT |
| 32 | 45 | NT | NT | 111 | 61* | NT | NT |
| 33 | 96 | NT | NT | 112 | 68* | NT | NT |
| 34 | 99 | 100 | NT | 113 | 66* | NT | NT |
| 35 | 71 | NT | NT | 114 | 53* | NT | NT |
| 36 | 98 | NT | NT | 115 | 37† | NT | NT |
| 37 | 73 | NT | NT | 116 | 8* | NT | NT |
| 38 | 87 | NT | NT | 117 | 75† | NT | NT |
| 39 | 100 | NT | NT | 118 | 90* | NT | NT |
| 40 | 93 | NT | NT | 119 | 75* | NT | NT |
| 41 | 86 | NT | NT | 120 | 0* | NT | NT |
| 42 | 91 | NT | NT | 121 | 98* | NT | NT |
| 43 | 95 | NT | NT | 122 | 94* | NT | NT |
| 44 | 60 | NT | NT | 123 | 82* | NT | NT |
| 45 | 98 | NT | NT | 124 | 100 | NT | NT |
| 46 | 100 | 100 | NT | 125 | 88* | NT | NT |
| 47 | 96 | NT | NT | 126 | 41* | NT | NT |
| 48 | 63* | NT | NT | 127 | 68* | NT | NT |
| 49 | 99 | NT | NT | 128 | 92* | NT | NT |
| 50 | 96 | NT | NT | 129 | 45* | NT | NT |
| 51 | 96 | NT | NT | 130 | 84* | NT | NT |
| 52 | 99 | NT | NT | 131 | 82* | NT | NT |
| 53 | 99 | NT | NT | 132 | 97* | NT | NT |
| 54 | 92 | NT | NT | 133 | 96* | NT | NT |
| 55 | 99 | NT | NT | 134 | 90* | NT | NT |
| 56 | 37 | NT | NT | 135 | 81* | NT | NT |
| 57 | 99 | NT | NT | 136 | 64* | NT | NT |
| 58 | 50* | NT | NT | 137 | 44* | NT | NT |
| 59 | 89 | NT | NT | 138 | 38* | NT | NT |
| 60 | 93 | NT | NT | 139 | 96* | NT | NT |
| 61 | 85 | NT | NT | 140 | 90* | NT | NT |
| 62 | 99 | NT | NT | 141 | 81* | NT | NT |
| 63 | 96 | NT | NT | 142 | 86* | NT | NT |
| 64 | 100 | NT | NT | 143 | 37* | NT | NT |
| 65 | 88 | NT | NT | 144 | 68* | NT | NT |
| 66 | 35* | NT | NT | 145 | 6* | NT | NT |
| 67 | 94 | NT | NT | 146 | 15* | NT | NT |
| 68 | 100 | NT | NT | 147 | 19* | NT | NT |
| 69 | 94* | NT | NT | 148 | 61* | NT | NT |
| 70 | 86* | NT | NT | 149 | 57* | NT | NT |
| 71 | 2* | NT | NT | 150 | 80* | NT | NT |
| 72 | 34* | NT | NT | 151 | 96* | NT | NT |
| 73 | 0 | NT | NT | 152 | >75* | NT | NT |
| 74 | 80 | NT | NT | 153 | 90* | NT | NT |
| 75 | 42 | NT | NT | 154 | 37* | NT | NT |
| 76 | 100 | NT | NT | 155 | 76* | NT | NT |
| 77 | 99 | NT | NT | 156 | 44* | NT | NT |
| 78 | 100 | NT | NT | 157 | 88* | NT | NT |
| 79 | 83* | NT | NT | 158 | 58* | NT | NT |
| 80 | 85* | NT | NT | 159 | >75* | NT | NT |
| 81 | 91 | NT | NT | 160 | >75* | NT | NT |
| 82 | 96 | NT | NT | 161 | 26* | NT | NT |
| 83 | 64* | NT | NT | 162 | 57* | NT | NT |
| 84 | 70* | NT | NT | 164 | 75* | NT | NT |
| 85 | 34* | NT | NT | 165 | 86* | NT | NT |
| 86 | 14* | NT | NT | 166 | 84* | NT | NT |
| 87 | 7* | NT | NT | 167 | 80* | NT | NT |

-continued

| Compound of Example No. | RT Assay % inhibition @ 10 μg/ml | T-Cell Assay % inhibition @ 3 μg/ml | Cytotoxicity Assay (EC$_{50}$, μM) |
|---|---|---|---|
| 168 | 90* | NT | NT |
| 169 | 42* | NT | NT |
| 170 | 86* | NT | NT |
| 171 | 92* | NT | NT |

\* = @ 1 μM
† = @ 1.25 μM
# = @ 0.5 μM
NT = not tested

EXAMPLES

The following examples further illustrate the present invention and will enable others skilled in the art to understand it more completely. It should be understood, however, that the invention is not limited to the particular examples given below.

Example 1

5,11-Dihydro-6H-dipyrido[3,2-b:2',3'-e][1,4]diazepin-6-one a) 2-Chloro-N-(2-chloro-3-pyridinyl)-3-pyridinecarboxamide In a three-necked round-bottomed flask, fitted with an efficient reflux condenser, mechanical stirrer and dropping funnel, were placed 215 g (1.672 mol) of 3-amino-2-chloropyridine, dissolved in a mixture of 400 ml dioxane, 500 ml cyclohexane and 130 ml pyridine. The solution of 299.2 g (1.7 mol) of freshly prepared 2-chloro-3-pyridinecarboxylic acid chloride in 200 ml dioxane was added at such a rate as to keep the vigorous reaction under control. Thereafter, the reaction mixture was allowed to cool to room temperature and the resulting crystalline precipitate was filtered off and washed successively with cyclohexane and ether.

The dark brown product was dissolved in 5 l of a 3% aqueous solution of sodium hydroxide. The resulting solution was treated with charcoal, suction filtered, and the filtrate was acidified by addition of 50% aqueous acetic acid. The resulting precipitate was collected by filtration and thoroughly washed with water. After being dried overnight in a stream of nitrogen at room temperature the almost colorless product had a m.p. of 156°–159° C. and was sufficiently pure for further reactions. The yield was 376.0 g (84% of theory).

b) N-(2-Chloro-3-pyridinyl)-2-[[(4-methoxyphenyl)methyl]amino]-3-pyridinecarboxamide 13.4 g (0.05 mol) of the product obtained in step a) were dissolved in 20 ml of xylene, and the resulting solution was admixed with 13.8 g (0.1 mol) of p-methoxybenzylamine. Thereafter, the mixture was refluxed for two hours. The reaction mixture was then evaporated in vacuo, and the residue was purified by column chromatography on silica gel (0.2–0.5 mm) using dichloromethane/ethyl acetate 10/1 (v/v) as an eluent. Concentration afforded colorless crystals, melting at 122°–124° C. (after recrystallization from acetonitrile). The yield was 17.2 g (93% of theory).

c) 5,11-Dihydro-11-[(4-methoxyphenyl)methyl]-6H-dipyrido[3,2-b:2',3'-e][1,4]diazepin-6-one 16.7 g (0.0453 mol) of the product obtained in step b) were dissolved in 150 ml of absolute dioxane, and the resulting solution was admixed with 6.7 g (0.14 mol) of a 50% dispersion of sodium hydride in mineral oil. Thereafter, the mixture—while protected against the external atmosphere by a low flow of nitrogen—was refluxed until no starting material could be detected by TLC. The surplus of sodium hydride was decomposed by cautious addition of 10 ml of a mixture of methanol and tetrahydrofuran (50/50 v/v). The reaction mixture was neutralized by addition of acetic acid and then was evaporated in vacuo. The residue was purified by column chromatography on silica gel (0.2–0.5 mm) using successively dichloromethane/ethyl acetate 10/1 (v/v) and dichloromethane/ethyl acetate 1/1 (v/v) as eluents. The crystalline product obtained by evaporation of suitable fractions was recrystallized from acetonitrile and 2-propanol. The product had a m.p. of 213°–215° C. and was identified as 5,11-dihydro- 11-[(4-methoxyphenyl)-methyl]-6H-dipyrido[3,2-b:2',3'-e][1,4]diazepin-6-one. The yield was 10.3 g (68% of theory).

d) 5,11-Dihydro-6H-dipyrido[3,2-b:2',3'-e][1,4]diazepin-6-one 10.0 g (0.3 mol) of the product obtained in step c) were dissolved in 50 ml of trifluoroacetic acid, whereby the mixture became slightly warm. Thereafter, the reaction mixture was stirred at 60° C. for 1 hour. No starting material could be detected by TLC at that time. The mixture was then evaporated in vacuo. The residue thus obtained was thoroughly stirred with 0.5% aqueous ammonia and then was filtered by suction. The raw product was recrystallized from 150 ml of dimethyl sulfoxide to provide colorless crystals of m.p. >340° C. The yield was 4.8 g (75% of theory). The product was identified as 5,11-dihydro-6H-dipyrido[3,2-b:2',3'-e][1,4]diazepin-6-one.

Example 2

5,11-Dihydro-11-propyl-6H-dipyrido[3,2-b:2',3'-e][1,4]diazepin-6-one a) N-(2-Chloro-3-pyridinyl)-2-(propylamino)-3-pyridinecarboxamide 26.8 g (0.1 mol) of 2-chloro-N-(2-chloro-3-pyridinyl)-3-pyridinecarboxamide were dissolved in 200 ml of dioxane, and the resulting solution was admixed with 21.4 g (0.362 mol) of propylamine. Thereafter, the mixture was shaken in a stainless steel pressure vessel at 150° C. for 6 hours. The reaction mixture was then evaporated in vacuo, and the residue was purified by column chromatography on silica gel, successively using dichloromethane/ethyl acetate 10/1 (v/v) and dichloromethane/cyclohexane/ethyl acetate 1/2/1 (v/v/v) as eluents. The product obtained by evaporation was a highly viscous resin that had a satisfactory quality for the following reaction.

b) 5,11-Dihydro-11-propyl-6H-dipyrido[3,2-b:2',3'-e][1,4]diazepin-6-one

Using a procedure analogous to that described in Example 1c), 5,11-dihydro-11-propyl-6H-dipyrido[3,2-b:2',3'-e][1,4]diazepin-6-one, m.p. 184°–186° C. (recrystallized from acetonitrile), was prepared from the product obtained in the above step a) and sodium hydride. The yield was 74% of theory.

Example 3

5,11-Dihydro-5-methyl-11-propyl-6H-dipyrido[3,2-b:2',3'-e][1,4]-diazepin-6-one a) 2-Chloro-N-(2-chloro-3-pyridinyl)-N-methyl-3-pyridinecarboxamide A four-necked round-bottomed flask, equipped with a mechanical stirrer, a dropping funnel, a thermometer and an efficient reflux condenser, was charged with 268.1 g (1.0 mol) of 2-chloro-N-(2-chloro-3-pyridinyl)-3-pyridinecarboxamide, 260 ml of 50% aqueous sodium hydroxide, 1500 ml of toluene and 8.0 g (0.0352 mol) of benzyltriethylammonium chloride. Stirring was begun and a solution of 134 ml (178.5 g, 1.415 mol) of dimethyl sulphate in 1 l of toluene was added dropwise over a period of about 3 hours, whereby the temperature rose to 50°–60° C. After the addition of dimethyl sulfate was complete, stirring at 60° C. was continued for a further 2 hours. The reaction mixture was cooled to room temperature and 1 l of water was added. The layers were separated, and the aqueous phase was extracted three times with 300-ml portions of toluene. The organic layers were combined and washed successively with 300 ml of water, 300 ml of 1% aqueous acetic acid and 300 ml of water. The combined organic extracts were dried over sodium sulfate, and the solvent was removed by distillation under reduced pressure. The residue was purified by column chromatography on silica gel (0.2–0.5 mm) using as eluents successively toluene and ethyl acetate/cyclohexane/tetrahydrofuran 1/9/10 (v/v/v). The product obtained by evaporation of suitable fractions was recrystallized from acetonitrile/tert-butyl methyl ether 1/1 (v/v). It was highly soluble in dichloromethane, had a m.p. of 98°–101° C., and was identified to be 2-chloro-N-(2-chloro-3-pyridinyl)-N-methyl-3-pyridinecarboxamide. The yield was 232.5 g (82.5% of theory).

b) N-(2-Chloro-3-pyridinyl)-N-methyl-2-(propylamino)-3-pyridinecarboxamide

Using a procedure analogous to that described in Example 2a, N-2-(chloro-3-pyridinyl)-N-methyl-2-(propylamino)-3-piperidinecarboxamide was prepared from the product obtained in the preceding step and propylamine. The yield was 91% of theory.

c) 5,11-Dihydro-5-methyl-11-propyl-6H-dipyrido[3,2-b:2′,3′-e][1,4]diazepin-6-one Using a procedure analogous to that described in Example 1c, except employing tetrahydrofuran instead of dioxane as a solvent and applying only equimolar quantities of sodium hydride, 5,11-dihydro-5-methyl-11-propyl-6H-dipyrido-[3,2-b:2′,3′-e][1,4[diazepin-6-one, a highly viscous oil, was prepared from the product obtained in the above step. The yield was 75% of theory.

Example 4

5,11-Diethyl-5,11-dihydro-6H-dipyrido[3,2-b:2′,3′-e][1,4]-diazepin-6-one 6.4 g (0.03 mol) of 5,11-dihydro-6H-dipyrido[3,2-b:2′,3′-e][1,4]diazepin-6-one were dissolved in 100 ml of absolute dimethylformamide, and the resulting solution was admixed with 3.4 g (0.071 mol) of a 50% dispersion of sodium hydride in mineral oil. While protected against the external atmosphere by a flow of nitrogen, the mixture was stirred at 50°–70° C. for 1 hour. After the evolution of hydrogen had ceased, the mixture was cooled to 30° C. and 10.9 g (0.07 mol) of ethyl iodide were added dropwise within 15 minutes. For completion of the exothermic reaction, the mixture was heated at 80°–90° C. for a further hour. The solvent was removed by distillation under reduced pressure. The residue was admixed with water and the suspension thus obtained was exhaustively extracted with dichloromethane. The product obtained after usual work-up was recrystallized from 150 ml of isooctane. The product had a m.p. of 102°–103° C. and was identified as 5,11-diethyl-5,11-dihydro- 6H-dipyrido[3,2-b:2′,3′-e][1,4]diazepin-6-one. The yield was 5.7 g (71% of theory).

Example 5

5,11-Dihydro-5-ethyl-6H-dipyrido[3,2-b:2′,3′-e][1,4]diazepin-6-one a) N-(2-Chloro-3-pyridinyl-2-[(phenylmethyl)amino]-3-pyridinecarboxamide Using a procedure analogous to that described in Example 1b, except employing diethyleneglycoldimethyl ether as a solvent instead of xylene, N-(2-chloro-3-pyridinyl)-2-[(phenylmethyl)amino]-3-pyridine carboxamide, m.p. 95°–97° C. (recrystallized from diethyleneglycoldimethyl ether), was prepared from 2-chloro-N-(2-chloro-3-pyridinyl)-3-pyridinecarboxamide and benzylamine. The yield was 72% of theory.

b) 5,11-Dihydro-11-(phenylmethyl)-6H-dipyrido[3,2-b:2′,3′-e][1,4]diazepin-6-one

Using a procedure analogous to that described in Example 1c except employing diethyleneglycoldimethyl ether as a solvent instead of dioxane, 5,11-dihydro-11-(phenylmethyl)-6H-dipyrido[3,2-b:2′,3′-e][1,4]-diazepin-6-one, m.p. 212°–213° C. (recrystallized from 1-propanol), was prepared from the product obtained in step a) and sodium hydride. The yield was 61% of theory.

c) 5,11-Dihydro-5-ethyl-11-(phenylmethyl)-6H-dipyrido-[3,2-b:2′,3′-e][1,4]diazepin-6-one Using a procedure analogous to that described in Example 3a, 5,11-dihydro-5-ethyl-11-(phenylmethyl)-6H-dipyrido[3,2-b:2′,3′-e][1,4]diazepin-6-one, m.p. 209°–211° C. (recrystallized from toluene/acetonitrile 1/1 v/v), dichloromethane/methanol 99/1 v/v), was prepared from the product obtained in step b) and diethyl sulfate. The yield was 82% of theory.

d) 5,11-Dihydro-5-ethyl-6H-dipyrido[3,2-b:2′,3′-e][1,4]diazepin-6-one

Using a procedure analogous to that described in Example 1d, except employing a pressure vessel instead of an open one and heating the mixture at 120° C. for 10 hours, 5,11-dihydro-5-ethyl-6H-dipyrido[3,2-b:2′,3′-e][1,4]diazepin-6-one, m.p. 161°–163° C. (recrystallized from isooctane/ethyl acetate 1/1 v/v), was prepared from the product obtained in step (c). The yield was 57% of theory.

Example 6

5,11-Dihydro-5-methyl-6H-dipyrido[3,2-b:2′,3′-e][1,4]diazepin-6-one a) N-(2-Chloro-3-pyridinyl)-N-methyl-2-[(phenylmethyl)amino]-3-pyridinecarboxamide Using a procedure analogous to that described in Example 1b, N-(2-chloro-3-pyridinyl)-N-methyl-2-[(phenylmethyl)amino]-3-pyridinecarboxamide, m.p. 114°–116° C. (recrystallized from tert-butyl methyl ether), dichloromethane/ethyl acetate 3/1 v/v), was prepared from 2-chloro-N-(2-chloro-3-pyridinyl)-N-methyl-3-pyridinecarboxamide and benzylamine. The yield was 87% of theory.

b) 5,11-Dihydro-5-methyl-11-(phenylmethyl)-6H-dipyrido[3,2-b:2′,3′-e][1,4]diazepin-6-one Using a procedure of analogous to that described in Example 3b, 5,11-dihydro-5-methyl-11-(phenylmethyl)-6H-dipyrido[3,2-b:2′,3′-e][1,4]diazepin-6-one, m.p. 198°–199° C. (recrystallized from acetonitrile), was prepared from the product obtained in step (a). The yield was 80% of theory.

c) 5,11-Dihydro-5-methyl-6H-dipyrido[3,2-b:2',3'-e][1,4]diazepin-6-one

A mixture consisting of 75.5 g (0.239 mol) of the product obtained in step b), 2.5 kg of polyphosphoric acid, and 425 ml of anisole was stirred at 140°–160° C. for 2 hours. While still hot, the reaction mixture was stirred into crushed ice. Thereafter, the mixture was made slightly alkaline by addition of aqueous ammonia and was then exhaustively extracted with dichloromethane. The combined organic layers were dried over sodium sulfate and evaporated in vacuo. The residue was chromatographed on silica gel using dichloromethane/ethyl acetate 1/1 (v/v) as an eluent. The product obtained by evaporation of suitable fractions was recrystallized from acetonitrile, yielding 21.6 g (40% of theory) of colorless crystals having a m.p. of 236°–237° C.

Example 7

5,11-Dihydro-6H-dipyrido[3,2-b:2',3'-e][1,4]diazepin-6-one 3.8 g (0.0126 mol) of the product obtained in Example 5b were dissolved in 20 ml of trifluoroacetic acid whereby the mixture became slightly warm. Thereafter, the reaction mixture was refluxed for 8 hours. No starting material could be detected by TLC at that point of time. The mixture was then evaporated in vacuo, the residue thus obtained was thoroughly stirred with 0.5% aqueous ammonia and then filtered by suction. The raw material was suspended in 20 ml of acetonitrile, refluxed for 15 minutes and suction filtered while hot. The filter cake was recrystallized from hot dimethyl sulfoxide yielding 1.2 g (45% of theory) of colorless crystals which had a m.p. >340° C. and were identified by m.p., mixed m.p. and UV-, IR- and MS spectra to be identical with the compound obtained in Example 1d.

Example 8

5,11-Dihydro-11-ethyl-5-methyl-6H-dipyrido[3,2-b:2',3'-e][1,4]diazepin-6-one a) 2-Chloro-N-(2-chloro-3-pyridinyl)-3-pyridinecarboxamide Using a procedure analogous to that described in Example 1a, 2-chloro-N-(2-chloro-3-pyridinyl)-3-pyridinecarboxamide was prepared. The purified product was obtained by cooling the reaction mixture to room temperature and decanting the supernatant from the precipitate. The solid was then dissolved in methylene chloride, and the solution washed with water, dried (anhydrous sodium sulfate), and the solvent removed in vacuo. The solid was then washed with ethyl acetate and dried to provide 7.24 g (84% of theory) of product suitable for use in the next reaction.

b) N-(2-Chloro-3-pyridinyl)-2-[[(4-methoxyphenyl)methyl]amino]-3-pyridinecarboxamide Using a procedure analogous to that described in Example 1b, N-(2-chloro-3-pyridinyl)-2-[[(4-methoxyphenyl)methyl]amino]-3-pyridinecarboxamide was prepared. The purified product was obtained by removing the solvent in vacuo, adding water to the residue, and extracting the product with methylene chloride. This solution was dried (anhydrous sodium sulfate) and the solvent removed to give a brown oil which was treated with 10 ml of ether. The product which crystallized was filtered and washed sequentially with ether and hexane to give 78.0 g (91% of theory) of the title compound as an off-white powder, m.p. 121°–122° C.

c) 5,11-Dihydro-11-[(4-methoxyphenyl)methyl]-6H-dipyrido[3,2-b:2',3'-e][1,4]diazepin-6-one 1.44 g of a 50% dispersion of sodium hydride in mineral oil was added to a solution of 3.69 g (0.010 mol) N-(2-chloro-3-pyridinyl)-2-[[(4-methoxyphenyl)methyl]amino]-3-pyridinecarboxamide in 100 ml of dimethylformamide. After the evolution of hydrogen stopped, the mixture was heated (110° C.) for 16 hours and then refluxed for eight hours. After the mixture had cooled, the excess sodium hydride was decomposed by the slow addition of ice. The mixture was further diluted with water, and the product was extracted with ether and concentrated. The crystallized residue was filtered and washed with ether to give 1.60 g of 5,11-dihydro-11-[(4-methoxyphenyl)methyl]-6H-dipyrido[3,2-b:2',3'-e][1,4]diazepin-6-one (50% of theory) as an off-white powder, m.p. 209°–210° C.

d) 5,11-Dihydro-11-[(4-methoxyphenyl)methyl]-5-methyl-6H-dipyrido [3,2-b:2',3'-e][1,4]diazepin-6-one 10.0 g (0.030 mol) of 5,11-dihydro-11-[(4-methoxyphenyl)methyl]-6H-dipyrido-[3,2-b:2',3'-e][1,4]diazepin-6-one was added to a flask containing 2.16 g of a 50% dispersion of sodium hydride in mineral oil and 100 ml of dimethylformamide. The resulting mixture was stirred at room temperature for 30 min. and then heated to 50° C. for 30 min. After cooling, 8.51 g (0.060 mol) of methyl iodide in 10 ml of dimethylformamide was added dropwise and the mixture was allowed to stir at room temperature overnight. Excess sodium hydride was decomposed by the careful addition of ice. Water was then added, and the product was extracted with ether, dried (anhydrous sodium sulfate), and concentrated to give 10.3 g (99% of theory) of 5,11-dihydro-11-[(4-methoxy-phenyl)-methyl]-5-methyl-6H-dipyrido-[3,2-b:2',3'-e][1,4]diazepin-6-one as a light yellow oil suitable for use in the next reaction.

e) 5,11-Dihydro-5-methyl-6H-dipyrido[3,2-b:2',3'-e][1,4]diazepin-6-one 50 ml of trifluoroacetic acid was added to 10.3 g (0.030 mol) of 5,11-dihydro-11-[(4-methoxyphenyl)methyl]-5-methyl-6H-dipyrido [3,2-b:2',3'-e][1,4]-diazepin-6-one, and the mixture was stirred for one hour at room temperature. The acid was removed in vacuo and the residue was stirred for one hour with 0.5% ammonia. The solid was filtered and dried to give 6.70 g (98% of theory) of pure 5,11-dihydro-5-methyl-6H-dipyrido[3,2-b:2',3'-e][1,4]diazepin-6-one, m.p. 230°–232° C.

f) 5,11-Dihydro-11-ethyl-5-methyl-6H-dipyrido[3,2-b:2',3'-e][1,4]diazepin-6-one 2.00 g of a 50% dispersion of sodium hydride in mineral oil was added to a solution of 5.75 g (0.025 mol) of 5,11-dihydro-5-methyl-6H-dipyrido[3,2-b:2',3'-e][1,4]diazepin-6-one in 100 ml of dimethylformamide. When the evolution of hydrogen ceased, the mixture was heated to 50° C. for 30 min. and then cooled to room temperature. Then, 7.80 g of ethyl iodide (neat) was added dropwise over 15 minutes, and the resulting mixture was allowed to stir overnight at room temperature. The excess sodium hydride was decomposed by the careful addition of ice, followed by water. The product was extracted with ether, dried (anhydrous sodium sulfate), and evaporated to yield 4.5 g (70% of theory) of 5,11-dihydro-11-ethyl-5-methyl-6H-dipyrido[3,2-b:2':3'-e][1,4]diazepin-6-one, m.p. 130°–132° C.

Example 9

5,11-Dihydro-11-ethyl -5-methyl -6H-dipyrido[3.2-b:2',3',-e][1,4]diazepin-6-thione A mixture of 2.66 g (0.01 mol) of 5,11-dihydro-11-ethyl-5-methyl-6H-dipyrido-[3,2-b:2'3'-e] [1,4]diazepin-6-one and 2.10 g (0.005 mol) of Lawesson's reagent (2,4-bis(4-methoxyphenyl)-1,3-dithia-2,4-diphosphetane-2,4-disulfide) in 50 ml of toluene was refluxed for 2½ h. The solvent was then removed in vacuo and water was added to the residue. The product was extracted with ethyl acetate, dried (anhydrous sodium sulfate), and concentrated in vacuo. Purification was effected on a silica gel column using methylene chloride as the first eluent, followed by ethyl acetate/hexane (1:4). Removal of the solvent in vacuo gave 2.20 g (74% of theory) of 5,11-dihydro-11-ethyl-5-methyl-6H-dipyrido[3,2-b:2',3'-e][1,4]diazepin-6-thione as a yellow powder, which was recrystallized from 10% hexane/ethyl acetate to provide 1.1 g of the title compound as yellow needles, m.p. 157°–158° C.

Example 10

5,11-Dihydro-11-ethyl-2-methyl-4-trifluoromethyl-6H-dipyrido-[3,2-b:2',3'-e][1,4]diazepin-6-one a) 3-Cyano-2-hydroxy-6-methyl-4-(trifluoromethyl)-pyridine A solution of 14.0 g of cyanoacetamide in 80 ml of ethanol was warmed to 50° C., and then 14 g of piperidine and 25 g of trifluoroacetylacetone were added. The resulting mixture was stirred at 70° for 30 min. and then allowed to stir overnight at room temperature. The mixture was concentrated in vacuo and then diluted with 100 ml of water. Concentrated hydrochloric acid (15 ml) was cautiously added with stirring and after 15 min. the precipitate was filtered and dried in vacuo overnight to give 27.8 g of the desired cyanopyridine.

b) 3-Aminocarbonyl-2-chloro-6-methyl-4-(trifluoromethyl)pyridine

A mixture of 35 ml of phosphorous oxychloride and 9.8 g of the cyanopyridine obtained above was refluxed for 5 hrs. The cooled mixture was quenched by cautiously adding to 400 ml of ice water. The product was extracted with methylene chloride, washed with saturated sodium bicarbonate, and dried (magnesium sulfate). After filtering and concentrating in vacuo, the crude chloro compound was dissolved in 50 ml of concentrated sulfuric acid and heated to 140° C. for 20 min. The cooled mixture was carefully poured over 600 ml of ice and the precipitate filtered, washed with ice water, and dried to give 7.6 g of the desired amide. The filtrate was extracted with 200 ml of ethyl acetate, dried (magnesium sulfate), filtered and concentrated to give an additional 1.7 g of product.

c) 3-Amino-2-chloro-6-methyl-4-(trifluoromethyl)pyridine

To a solution of 6.6 g of sodium hydroxide in 60 ml of water at 5° C. was added 9.3 g of bromine. When a clear solution was obtained, 9.2 g of 3-aminocarbonyl-2-chloro-6-methyl-4-(trifluoromethyl)pyridine was added quickly, maintaining the temperature below 5° C. The resulting mixture was stirred until the 3-(aminocarbonyl)pyridine dissolved (~30 min). The cooling bath was removed and the mixture was then warmed to 75° C. for 30 min. After cooling to room temperature, the 3-aminopyridine product was extracted with ethyl acetate, dried (magnesium sulfate), filtered, and evaporated to give 4.9 g of the desired product.

d) 2-Chloro-N-(2-chloro-6-methyl-4-trifluoromethyl-3-pyridinyl)-3-pyridinecarboxamide To a cooled (−78° C.) solution of 2.1 g of the 3-amino-2-chloro-6-methyl-4-(trifluoromethyl)pyridine in 10 ml of THF was added dropwise over 3 min. 7 ml of lithium diisopropylamine (LDA, 1.5M in cyclohexane). The mixture was stirred 5 min., and 0.9 g of 2-chloronicotinoyl chloride in 3 ml of THF was added over 1 min. After 5 min. an additional 3 ml of LDA solution was added followed by an additional 0.5 g of the acid chloride in 1 ml of THF. The resulting mixture was stirred 10 min. and then quenched with 100 ml of water. After partitioning with 30 ml of ethyl acetate, the organic phase was extracted with water and the combined aqueous phases extracted with methylene chloride, dried (magnesium sulfate), filtered and evaporated to give the crude product. This was washed with a small amount of ethyl acetate and dried to give 1.3 g of the title compound.

e) N-(2-Chloro-6-methyl-4-trifluoromethyl-3-pyridinyl)-2-ethylamino-3-pyridinecarboxamide Ethylamine (0.4 g) was added to a suspension of 1.3 g of 2-chloro-N-(2-chloro-6-methyl-4-trifluoromethyl-3-pyridinyl)-3-pyridinecarboxamide in 5 ml of xylene, and the resulting mixture heated in a pressure tube for 30 min. at 160° C. The cooled mixture was diluted with ethyl acetate, washed, dried, and concentrated. Column chromatography over silica gel (ethyl acetate/hexane, 1:1) gave 0.5 g of the title compound.

f) 5,11-Dihydro-11-ethyl-2-methyl-4-trifluoromethyl-6H-dipyrido-[3,2-b:2',3'-e][1,4]diazepin-6-one A solution of 0.5 g of N-(2-chloro-6-methyl-4-trifluoromethyl-3-pyridinyl)-2-ethylamino-3-pyridinecarboxamide in 3 ml of pyridine was added to 0.2 g of a 50% dispersion of sodium hydride in oil. The mixture was heated to 150° C. and then cooled and concentrated in vacuo. Water was added to the residue and the product was extracted with ethyl acetate, dried (magnesium sulfate), filtered, and concentrated. The product was purified by column chromatography over silica gel (methylene chloride, then methylene chloride/methanol). After concentrating in vacuo, the residue was crystallized from hexane to give 0.09 g of the title compound, m.p. 150°–151° C.

Example 11

5,11-Dihydro-11-ethyl-4-methyl-6H-dipyrido[3,2-b:2',3'-e][1,4]diazepin-6-one a) 2-Chloro-4-methyl-3-nitropyridine A mixture of 25 g of 2-hydroxy-4-methyl-3-nitropyridine, 12.5 g of phosphorous pentachloride, and 62 ml of phosphorous oxychloride was refluxed for 2 hrs. After cooling, the mixture was poured onto crashed ice and stirred until a precipitate formed. The product was extracted with methylene chloride, dried (sodium sulfate) and concentrated to a brown oil, which was washed with hot hexane. Concentration in vacuo provided 16.2 g of the the the title compound, m.p. 45°–47° C.

b) 3-Amino-2-chloro-4-methylpyridine 16.2 g of 2-chloro-4-methyl-3-nitropyridine was added to 470 ml of acetic acid and the resulting mixture stirred at room temperature for 15 min. A solution of 160 g of stannic chloride dihydrate in 200 ml of concentrated hydrochloric acid was then added in one portion and the resulting mixture stirred overnight at room temperature. This mixture was then diluted to 1 liter with water and 10N sodium hydroxide was added slowly with cooling until the white precipitate of tin hydrochloride dissolved. The product was extracted with methylene chloride, dried (sodium sulfate) and concentrated to give 12.8 g of a yellow oil, which solidified on standing, of almost pure 3-amino-2-chloro-4-methylpyridine suitable for use in the next reaction.

c) 2-Chloro-N-(2-chloro-4-methyl-3-pyridinyl)-3-pyridinecarboxamide

Using a procedure analogous to that described in Example 1a, the carboxamide was prepared from 12.8 g of 3-amino-2-chloro-4-methyl pyridine, 15.8 g of 2-chloronicotinoyl chloride, 7.1 g of pyridine, 30 ml of cyclohexane and 60 ml of dioxane. After removal of the solvent, the product was dissolved in methylene chloride, washed with water and dried (sodium sulfate). After removal of the solvent, the residue was washed with ethyl acetate to give 1.2 g of the title compound, m.p. 193°–194° C.

d) N-(2-Chloro-4-methyl-3-pyridinyl)-2-ethylamino-3-pyridinecarboxamide

Ethylamine (12.7 g) was added to a suspension of 21.0 g of the 2-chloro-N-(2-chloro-4-methyl-3-pyridinyl)-3-pyridinecarboxamide in 150 ml of xylene in a steel bomb. The mixture was then heated in an oil bath to 165° C. for 6 hrs. and then stirred overnight at room temperature. The solvent was removed in vacuo and water added to the residue. The product was extracted with ether, dried (sodium sulfate) and concentrated to give an oil. This was dissolved in ethyl acetate followed by hexane at which time a precipitate formed. The solid was filtered and dried to give 16.5 g of the title compound, m.p. 122°–124° C.

e) 5,11-Dihydro-11-ethyl-4-methyl-6H-dipyrido[3,2-b:2',3'-e][1,4]diazepin-6-one

A 50% suspension of sodium hydride (7.9 g) was added to a solution of 16.0 g of N-(2-chloro-4-methyl-3-pyridinyl)-2-ethylamino-3-pyridinecarboxamide obtained above in 200 ml of dimethylformamide and stirred for 30 min. The mixture was then refluxed for 2 hrs., cooled and carefully treated with crushed ice. The solvent was removed in vacuo and water was added to the residue. The product was extracted with ether, dried (sodium sulfate) and concentrated. The residue was boiled with ethyl acetate/cyclohexane (1:1) and filtered to give 4.1 g of almost pure product. 2.0 g of this product was further purified by recrystallization from dichloroethane to give 1.0 g of pure 5,11-dihydro-11-ethyl-4-methyl-6H-dipyridol[3,2b:2',3'-e][1,4]diazepin-6-one, m.p. 212°–214° C.

Example 12

11-Cyclopropyl-5,11-dihydro-4-methyl-6H-dipyrido[3,2-b:2',3'-e][1,4]diazepin-6-one Using a procedure analogous to that employed in Example 11, but using cyclopropylamine instead of ethylamine, yielded the title compound, m.p. 247°–249° C.

Example 13

11-Cyclopropyl-5,11-dihydro-5-hydroxy-4-methyl-6H-dipyrido[3,2-b:2',3'-e][1,4]diazepin-6-one To a mixture of 0.5 g of 11-cyclopropyl-5,11-dihydro-4-methyl-6H-dipyrido[3,2-b:2',3'-e][1,4]diazepin-6-one (Example 12) in 25 ml of tetrahydrofuran was added 0.12 g of 50% sodium hydride in mineral oil. The reaction mixture was stirred at room temperature for one hour and then cooled to 0° C., at which time 0.9 g of oxodiperoxymolybdenum(pyridine)hexamethylphosphoramide (MoOPH) was added in one portion. The reaction mixture was then allowed to warm to room temperature and was allowed to stir overnight. The mixture was quenched with water and the solvents removed in vacuo. The residue was extracted with warm ethyl acetate, concentrated in vacuo and purified on a silica gel column (eluent: ethyl acetate) to give 0.05 g of pure 11-cyclopropyl-5,11-dihydro-5-hydroxy-4-methyl-6H-dipyrido[3,2-b:2',3'-e][1,4]diazepin-6-one, m.p. 239°–241° C. The yield was 9.5% of theory.

Example 14

5,11-Dihydro-11-ethyl-2-methoxy-5-methyl-6H-dipyrido[3,2-b:2',3'-e][1,4]diazepin-6-one a) 3-Amino-2-bromo-6-methoxypyridine Sodium acetate (1.6 g) was added to a solution of 5-amino-2-methoxypyridine (2.5 g) in acetic acid (15 ml). To the resulting solution bromine (3.0 g) was added dropwise, and the mixture was stirred for 20 min., and then added to a solution of sodium hydroxide (10 g) in water (100 ml). The product was extracted with ethyl acetate (50 ml), dried (anhydrous magnesium sulfate), and concentrated in vacuo. The product was purified over a silica gel column (ethyl acetate/hexane, 1:4) to give 2.7 g of the title compound, suitable for use in the next reaction.

b) N-(2-Bromo-6-methoxy-3-pyridinyl)-2-chloro-3-pyridinecarboxamide

To a solution of 3-amino-2-bromo-6-methoxypyridine (2.7 g) in methylene chloride (20 ml) and pyridine (1 ml) was added 2-chloronicotinoyl chloride (2.2 g), and the resulting mixture was stirred 20 min. The mixture was then diluted with methylene chloride (100 ml), washed with water (100 ml), dried (anhydrous magnesium sulfate), and concentrated. The semisolid residue was saturated with hexane, filtered, and dried to give 4.1 g of product suitable for use in the next reaction.

c) N-(2-Bromo-6-methoxy-3-pyridinyl)-2-chloro-N-methyl-3-pyridinecarboxamide

Sodium hydride (0.3 g of a 50% dispersion in mineral oil) was added to dimethylsulfoxide (10 ml) and warmed to 50° C. After cooling the mixture to room temperature. N-(2-bromo-6-methoxy-3-pyridinyl)-2-chloro-3-pyridinecarboxamide (2.0 g) was added and the resulting solution was stirred for 10 min. Methyl iodide (0.4 ml) was then added and the mixture was stirred for 30 min. The reaction mixture was quenched by the addition of water (10 ml) and ethyl acetate (100 ml) was then added. The organic phase was washed with water (4×100 ml), dried (anhydrous magnesium sulfate), concentrated, and purified on a silica gel column (methylene chloride followed by methylene chloride/ethanol, 98:2) to give 1.9 g of the title compound, suitable for use in the next reaction.

d) N-(2-Bromo-6-methoxy-3-pyridinyl)-2-ethylamino-N-methyl-3-pyridinecarboxamide Ethylamine (0.7 g) was added to a solution of N-(2-bromo-6-methoxy-3-pyridinyl)-2-chloro-N-methyl-3-pyridinecarboxamide (1.9 g) in xylene (5 ml), and the resulting mixture was sealed in a pressure bottle and heated at 150° C. for 4 hours. The solution was diluted with ethyl acetate, washed with water, dried (anhydrous magnesium sulfate), concentrated, and purified on a silica gel column (ethyl acetate/hexane, 1:4) to give 1.5 g of the title compound, suitable for use in the next reaction.

e) 5,11-Dihydro-11-ethyl-2-methoxy-5-methyl-6H-dipyrido[3,2-b:2',3'-e][1,4]diazepin-6-one Sodium hydride (0.9 g of a 50% dispersion in mineral oil) was added to a solution of N-(2-bromo-6-methoxy-3-pyridinyl)-2-ethylamino-N-methyl-3-pyridinecarboxamide (1.4 g) in xylene (20 ml) and the mixture refluxed for 2 hours. After cooling, the mixture was quenched with methanol, diluted with ethyl acetate, and washed with water. The organic phase was dried (anhydrous magnesium sulfate), concentrated, and purified on a silica gel column (ethyl acetate/hexane, 1:4) to give fairly pure product, which was then recrystallized twice from ethyl acetate/hexane to give 0.52 g of pure 5,11-dihydro-11-ethyl-2-methoxy-5-methyl-6H-dipyrido[3,2-b:2',3'-e][1,4]diazepin-6-one, m.p. 116°–118° C.

Example 15

5,11-Dihydro-11-ethyl-5-methyl-2-(N-pyrrolidino)-6H-dipyrido[3,2-b:2',3'-e][1,4]diazepin-6-one a) 5,11-Dihydro-11-ethyl-2-hydroxy-5-methyl-6H-dipyrido[3,2-b:2',3'-e][1,4]diazepin-6-one Hydrobromic acid (48%, 2 ml) was added to a solution of 5,11-dihydro-11-ethyl-2-methoxy-5-methyl-6H-dipyrido[3,2-b:2',3'-e][1,4]diazepin-6-one (0.3 g) in acetic acid (2 ml), and the resulting mixture was rapidly heated to reflux for 5 min. The reaction mixture was quenched with 10% sodium hydroxide (10 ml) and the product was extracted with ethyl acetate, dried (anhydrous magnesium sulfate) and concentrated to give a solid which was recrystallized from ethyl acetate to give 0.08 g of product, m.p. 215°–218° C.

b) 5,11-Dihydro-11-ethyl-5-methyl-2-trifluoromethanesulfonyloxy-6H-dipyrido[3,2-b:2',3'-e][1,4]diazepin-6-one To a solution of 5,11-Dihydro-11-ethyl-2-hydroxy-5-methyl-6H-dipyrido[3,2-b:2',3'-e][1,4]diazepin-6-one (0.2 g) in methylene chloride (4 ml) under nitrogen was added diisopropylethylamine (0.2 ml) followed by trifluoromethanesulfonic anhydride (0.2 ml). The resulting mixture was stirred for one hour, and then diluted with methylene chloride (20 ml), and washed with water. The organic phase was dried (anhydrous magnesium sulfate), concentrated, and purified on a silica gel column (ethyl acetate/hexane, 1:3) to give fairly pure product, suitable for use in the next reaction.

c) 5,11-Dihydro-11-ethyl-5-methyl-2-(N-pyrrolidino)-6H-dipyrido[3,2-b:2',3'-e][1,4]diazepin-6-one 5,11-Dihydro-11-ethyl-5-methyl-2-trifluoromethanesulfonyloxy-6H-dipyrido[3,2-b:2',3'-e][1,4]diazepin-6-one (0.25 g) was dissolved in pyrrolidine (1 ml) and refluxed 30 min. The cooled solution was diluted with ethyl acetate, washed with water, and the organic phase was dried (anhydrous magnesium sulfate) and concentrated. The resulting oily residue was crystallized from ethyl acetate/hexane to provide 0.11 g of 5,11-dihydro-11-ethyl-5-methyl-2-n-(pyrrolidino-6H-dipyrido[3,2-b:2',3'-e][1,4]diazepin-6-one, m.p. 185°–188° C.

Example 16

5,11-Dihydro-11-ethyl-2-methoxy-4-methyl-6H-dipyrido[3,2-b:2',3'-e][1,4]diazepin-6-one a) 2-Methoxy-4-methyl-5-nitropyridine Sodium methoxide (26.1 g) was added to a solution of 2-chloro-4-methyl-5-nitropyridine (19.0 g) in methanol (100 ml) and the resulting mixture was refluxed for 12 hours. Upon cooling, the mixture was poured over water (1 L), and the product was extracted with ethyl acetate and washed with water. The organic phase was dried (anhydrous magnesium sulfate) and concentrated, and the residue dissolved in hot ether and filtered. Crystallization from ether provided 10.2 g of the title compound, suitable for use in the next reaction.

b) 5-Amino-2-methoxy-4-methylpyridine

A mixture of stannous chloride dihydrate (41 g) and concentrated hydrochloric acid (40 ml) was added slowly to a solution of 2-methoxy-4-methyl-5-nitropyridine (5.1 g) in acetic acid (40 ml), maintaining the temperature below 35° C. The resulting mixture was stirred at room temperature for 2 hours, and then allowed to stand overnight in the refrigerator. The solid was collected and both solid and supernatant were separately basified with a 20% sodium hydroxide solution. The product was extracted with chloroform, combined, dried (anhydrous magnesium sulfate) and concentrated to give 3.9 g of the title compound as a solid, suitable for use in the next reaction.

c) 3-Amino-2-bromo-6-methoxy-4-methylpyridine

Bromine (4.8 g) was added in one portion to a mixture of 5-amino-2-methoxy-4-methylpyridine (3.9 g) in acetic acid (25 ml) and sodium acetate (4.0 g). The resulting mixture was stirred for 20 min. and then added to a solution of sodium hydroxide (15 g) in water (200 ml). The product was extracted with chloroform, dried (anhydrous magnesium sulfate), concentrated, and purified on a silica gel column (methylene chloride/ethyl acetate, 19:1→4:1) to give 4.5 g of the title compound, suitable for use in the next reaction.

d) N-(2-Bromo-6-methoxy-4-methyl-3-pyridinyl)-2-chloro-3-pyridinecarboxamide 2-Chloronicotinoyl chloride (3.5 g) was added to a solution of 3-amino-2-bromo-6-methoxy-4-methylpyridine (4.5 g) in methylene chloride, and the resulting mixture was stirred overnight at room temperature, and triturated with diisopropyl ether. The precipitated solid was filtered to give 6.0 g of the title compound, suitable for use in the next reaction.

e) N-(2-Bromo-6-methoxy-4-methyl-3-pyridinyl)-2-ethylamino-3-pyridinecarboxamide A mixture of N-(2-bromo-6-methoxy-4-methyl-3-pyridinyl)-2-chloro-3-pyridinecarboxamide (2.1 g), dioxane (10 ml), and ethylamine (0.5 g) was heated to 140° C. in a sealed tube for 5 hours. The cooled mixture was diluted with ethyl acetate, washed with water, and the organic phase was dried (anhydrous magnesium sulfate) and concentrated. The product was purified on a silica gel column (methylene chloride/ethyl acetate, 99:1) and crystallized by trituration with diisopropyl ether to give 0.95 g of the title compound.

f) 5,11-Dihydro-11-ethyl-2-methoxy-4-methyl-6H-dipyrido[3,2-b:2',3'-e][1,4]diazepin-6-one Sodium hydride (0.14 g of a 50% dispersion in mineral oil) was added to a solution of N-(2-bromo- 6-methoxy-4-methyl-3-pyridinyl)-2-ethylamino-3-pyridinecarboxamide (0.54 g) in pyridine (4 ml), and the resulting mixture was refluxed for 1.5 hours. The cooled mixture was diluted with ethyl acetate, washed with water, and the organic phase was dried (anhydrous magnesium sulfate) and concentrated. The residue was washed with diisopropyl ether and hot ethyl acetate, and then crystallized from ethanol to provide 0.2 g of 5,11-dihydro-11-ethyl-2-methoxy-4-methyl-6H- dipyrido[3,2-b:2',3'-e][1,4]diazepin-6-one m.p. 249°–251° C.

Examples 17–122

Using procedures analogous to those described above, the compounds of Examples 17–122, which are described below in Table II, were made.

TABLE II

Compounds in this table are of the formula

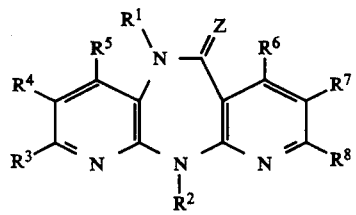

wherein $R^1$–$R^8$ are as defined below and Z is an oxygen atom unless noted to be a sulfur atom.

| Ex. | $R^1$ | $R^2$ | Other | m.p. (°C.) |
|---|---|---|---|---|
| 17 | H | ethyl | 4-chloro | 184–186 |
| 18 | H | ethyl | 4-ethyl | 218–219 |
| 19 | H | 4-methoxybenzyl | | 209–210 |
| 20 | methyl | ethyl | 8-chloro | 105–106 |
| 21 | H | ethyl | 2,4-dimethyl | 210–211 |
| 22 | methyl | ethyl | 3-chloro, 2-nitro | 215–216 |
| 23 | H | cyclobutyl | 4-methyl | 214–215 |
| 24 | H | isopropyl | 4-methyl | 188–189 |
| 25 | H | cyclopropyl | 2,4-dimethyl | >300 |
| 26 | H | ethyl | 3,4-dimethyl | 265–266 |
| 27 | H | cyclopropyl | 4-ethyl | 228–230 |
| 28 | H | ethyl | 2,4,9-trimethyl | 228–230 |
| 29 | H | ethyl | 2-chloro, 4-methyl | 224–228 |
| 30 | H | cyclopropyl | 2-chloro, 4-methyl | 310–320 |
| 31 | methyl | benzyl | | NA |
| 32 | methyl | 4-methoxybenzyl | | 120–121 |
| 33 | methyl | 2-fluoroethyl | | 117–118 |
| 34 | H | ethyl | | 211–212 |
| 35 | H | phenyl | | 220–222 |
| 36 | methyl | ethyl | 4-methyl | 157–159 |
| 37 | methyl | acetyl | | 138–143 |
| 38 | methyl | t-butyl | | 192–194 |
| 39 | H | ethyl | 2,3-dimethyl | 212–214 |
| 40 | methyl-thiomethyl | ethyl | | 118–120 |
| 41 | H | ethyl | 9-methyl | 244–247 |
| 42 | H | ethyl | 2-methyl | 263–266 |
| 43 | H | ethyl | 3-methyl | |
| 44 | H | acetyl | | >215 (dec) |
| 45 | methyl | ethyl | 2,9-dimethyl | 100–102 |
| 46 | methyl | ethyl | 2-methyl | 124–126 |
| 47 | methyl | ethyl | 3-methyl | 94–96 |
| 48 | methyl | ethyl | 8-azido | 265–266 |
| 49 | methyl | ethyl | 3,4-dimethyl | 119–120 |
| 50 | methyl | ethyl | 9-methyl | 79–93 |
| 51 | acetyl | ethyl | | 123–124 |
| 52 | H | isopropyl | | 204–206 |
| 53 | methyl | methylthiomethyl | | 109–110 |
| 54 | H | ethyl | 3-chloro | 217–218 |
| 55 | methyl | ethyl | 3-chloro | 124–125 |
| 56 | benzyl | acetyl | | 169–170 |
| 57 | H | cyclopropyl | | 240–250 |
| 58 | methyl | cyclopropyl | 4-methyl | 244–245 |
| 59 | H | ethyl | 8-methyl | 182–183 |
| 60 | methyl | cyclopropylmethyl | | 138–139 |
| 61 | H | (R)-2-butyl | | 172–174 |
| 62 | methyl | allyl | | 93–95 |
| 63 | H | ethyl | 2-chloro | 252–254 |
| 64 | methyl | ethyl | 2,3-dimethyl | 143–145 |
| 65 | H | (S)-2-butyl | | 173–175 |
| 66 | H | cyclopentyl | | 225–228 |

TABLE II-continued

Compounds in this table are of the formula

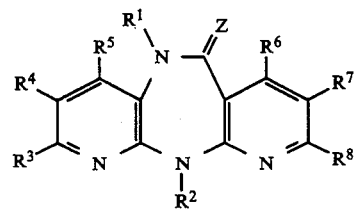

wherein $R^1$–$R^8$ are as defined below and Z is an oxygen atom unless noted to be a sulfur atom.

| Ex. | $R^1$ | $R^2$ | Other | m.p. (°C.) |
|---|---|---|---|---|
| 67 | methyl | propargyl | | 169–170 |
| 68 | methyl | ethly | 2-chloro | 125–126 |
| 69 | methyl | ethyl | 2-(pyrrolidin-1-yl), 4-methyl | 244–246 |
| 70 | methyl | ethyl | 2-(3-pyrrolin-1-yl) | 153–156 |
| 71 | H | ethyl | 7,9-dimethyl | 245–247 |
| 72 | methyl | cyclopentyl | | |
| 73 | methoxymethyl | methoxymethyl | 4-methyl | 135–137 |
| 74 | H | ethyl | 7-methyl | 193–194 |
| 75 | H | ethyl | 8,9-dimethyl | 204–206 |
| 76 | H | ethyl | 2-chloro, 4-trifluoromethyl | 158–160 |
| 77 | H | cyclobutyl | | 241–243 |
| 78 | methyl | cyclobutyl | | 144–146 |
| 79 | H | cyclopropyl | 4-chloro | NA |
| 80 | methyl | ethyl | 2-(tetrahydropyridin-1-yl) | 138–140 |
| 81 | H | cyclopropyl | 4-methoxy | 185–187 |
| 82 | H | ethyl | 4-methoxy | 156–157 |
| 83 | methyl | ethyl | 2-(p-methoxybenzylmethylamino) | 83–85 |
| 84 | methyl | ethyl | 2-allylamino | 167–170 |
| 85 | H | cyclopropyl | 4-hydroxymethyl | 243–246 |
| 86 | H | ethyl | 8-bromo | 233–235 |
| 87 | methyl | ethyl | 3-nitro | 154–156 |
| 88 | methyl | ethyl | 3,8-dinitro | 167–169 |
| 89 | methyl | ethyl | 3-amino | 235–240 |
| 90 | methyl | ethyl | 2,8-dinitro, 3-chloro | 215–216 |
| 91 | H | cyclopropyl | 4-methyl, 7-hydroxy | 225–227 |
| 92 | methyl | ethyl | 2,4-dimethyl | 151–153 |
| 93 | H | cyclopropyl | 4-methyl, (Z = S) | 189–194 |
| 94 | methyl | cyano | | 274–277 |
| 95 | methyl | cyclohexyl | | 145–146 |
| 96 | H | cyclohexyl | | 199–201 |
| 97 | H | ethyl | 7,9-dimethyl, 8-chloro | 160–162 |
| 98 | methyl | cyclopropyl | | 163–166 |
| 99 | methyl | methylsulfonyl | | 239–241 |
| 100 | methyl | ethyl | 2-amino, 3-chloro | 160–162 |
| 101 | allyl | cyclopropyl | 4-methyl | 146–149 |
| 102 | methyl | ethyl | 7-methyl | 122–124 |
| 103 | H | ethyl | 4-methyl, (Z = S) | 158–159 |
| 104 | H | ethyl | 4-hydroxy | 295–296 |
| 105 | methyl | ethyl | 3,8-diamino | 240–250 |
| 106 | methyl | ethyl | 2-hydroxy | 215–218 |
| 107 | H | ethyl | 2,4-dimethyl, (Z = S) | 199–201 |
| 108 | vinyloxycarbonyl | cyclopropyl | 4-methyl | 140–143 |
| 109 | methoxy | cyclopropyl | 4-methyl | 169–171 |
| 110 | acetyl | cyclopropyl | 4-methyl | 176–179 |
| 111 | methyl | ethyl | 2-(p-methoxybenzylamino) | 133–135 |
| 112 | methyl | ethyl | 2-(morpholin-1-yl) | 158–160 |
| 113 | methyl | ethyl | 2-(piperidin- | 164–166 |

TABLE II-continued

Compounds in this table are of the formula

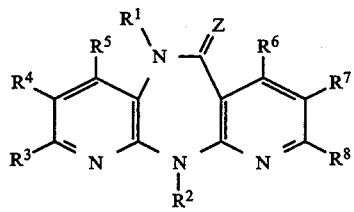

wherein R¹-R⁸ are as defined below and Z is an oxygen atom unless noted to be a sulfur atom.

| Ex. | R¹ | R² | Other | m.p. (°C.) |
|---|---|---|---|---|
| 114 | methyl | ethyl | 1-yl) 2-amino | 197–199 |
| 115 | H | cyclopropyl | 4-cyano | 243–245 |
| 116 | dimethyl- aminoethyl | cyclopropyl | | 88–89 |
| 117 | methyl | ethyl | 2-methylamino | 186–189 |
| 118 | methyl | ethyl | 2-(dimethyl- amino) | 118–120 |
| 119 | methyl | ethyl | 2-ethylamino | 154–157 |
| 120 | methyl | ethyl | 8-nitro | 148–149 |
| 121 | H | ethyl | 2-(dimethyl- amino), 4-methyl | 209–211 |
| 122 | H | ethyl | 2-(pyrrolidin-1- yl), 3-chloro, 4- methyl | 215–218 |

NA = not available

Example 123

8-Amino-5,11-dihydro-11-ethyl-5-methyl-6H-dipyrido[3,2-b:2',3'-e][1,4]diazepin-6-one hemihydrate a) 2-Ethylamino-3-nitropyridine A stirred mixture of 2-chloro-3-nitropyridine (8.60 g, 0.054 mol), ethylamine (5.37 g, 0.12 mol), and xylene (10 ml) was heated at 100° C. in a sealed tube for three hours. After cooling, the solvent was removed in vacuo, and water was added to the residue. The product was extracted with methylene chloride, dried (sodium sulfate), and concentrated in vacuo to give 10.0 g of the title compound as a yellow oil, suitable for use in the next reaction.

b) 3-Amino-2-ethylaminopyridine

Using a procedure analogous to that described in Example 11b, 6.5 g of the title compound was prepared from 9.1 g of 2-ethylamino-3-nitropyridine.

c) 2-Chloro-N-(2-ethylamino-3-pyridinyl)-5-nitro-3-pyridinecarboxamide

A solution of 2.21 g of 2-chloro-5-nitronicotinoyl chloride (obtained by nitrating 2-hydroxynicotinic acid, followed by conversion to 2-chloro-5-nitronicotinic acid, which was then treated with thionyl chloride) in 10 ml of tetrahydrofuran was slowly added over 15 minutes to a cooled, stirred mixture of 1.34 g of 3-Amino-2-ethylaminopyridine, 1.29 g of diisopropylethylamine, and 40 ml of tetrahydrofuran. The resulting mixture was allowed to stir overnight at room temperature, and then concentrated in vacuo. The title compound (2.30 g, m.p. 185°-186° C.), which precipitated out when the residue was treated with methylene chloride, was suitable for use in the next reaction.

d) 5,11-Dihydro-11-ethyl-8-nitro-6H-dipyrido[3,2-b:2',3'-e][1,4]diazepin-6-one

A solution of 1.80 g of 2-chloro-N-(2-ethylamino-3-pyridinyl)-5-nitro-3-pyridinecarboxamide in 25 ml of xylene was refluxed for four hours. After concentrating in vacuo, the residue was purified on a silical gel column eluting with 50% ethyl acetate/hexane to give 0.93 g of the title compound.

e) 5,11-Dihydro-11-ethyl-5-methyl-8-nitro-6H-dipyrido[3,2-b:2',3'-e][1,4]diazepin-6-one The title compound (0.72 g, m.p. 148°-149° C.) was prepared from 0.93 g of 5,11-dihydro-11-ethyl- 8-nitro-6H-dipyrido[3,2-b:2',3'-e][1,4]diazepin-6-one in a manner analogous to that described in Example 8d.

f) 8-Amino-5,11-dihydro-11-ethyl-5-methyl-6H-dipyrido[3,2-b:2',3'-e][1,4]diazepin-6-one hemi-hydrate Following a procedure analogous to that described in Example 11b, 0.23 g of 5,11-dihydro-11-ethyl-5-methyl-8-nitro-6H-dipyrido[3,2-b:2',3'-e][1,4]diazepin-6-one reduced to give, after recrystallization from 1,2-dichloroethane/hexane, 0.060 g of the title compound as a yellow-brown powder, m.p. 193°-194° C.

Example 124

6-Cyanoimino-5,11-dihydro-11-ethyl-2,4-dimethyl-6H-dipyrido[3,2-b:2',3'-e][1,4]diazepine A mixture of 5,11-dihydro-11-ethyl-6-methanesulfonyloxy-2,4-dimethyl-6H-dipyrido[3,2-b:2',3'-e][1,4]diazepine (0.25 g, 0.63 mmol), cyamamide (0.034 g, 0.8 mmol), 5 ml of 1,4-dioxane, and potassium carbonate (0.11 g, 0.8 mmol) was stirred at room temperature for 10 days. The mixture was then concentrated in vacuo, and the was residue partitioned between ethyl acetate and water. The organic phase was dried, filtered and concentrated in vacuo. The residue was chromatographed over silica with 10% ethyl acetate/methylene chloride to provide 0.025 g of the title compound, m.p. 230°-233° C.

Example 125

5,11-Dihydro-11-ethyl-6-methoxyimino-2,4-dimethyl-6H-dipyrido [3,2-b:2',3'-e][1,4]diazepine a) 5,11-Dihydro-11-ethyl-6-methanesulfonyloxy-2,4-dimethyl-6H-dipyrido[3,2-b:2',3'-e][1,4]diazepine Trifluoromethanesulfonic anhydride (0.24 ml, 14 mmol) was added to a solution of 0.314 g (1.2 mmol) 5,11-dihydro-11-ethyl-2,4-dimethyl-6H-dipyrido[3,2-b:2',3'-e][1,4]diazepin-6-one in 15 ml of methylene chloride containing 0.25 ml (14 mmol) of diisopropylethylamine, and the resulting mixture was refluxed under argon for three hours. Ethyl acetate (~200 mL) was then added and the solution was washed three times with water and four times with brine. After drying (magnesium sulfate), the solution was concentrated in vacuo and the residue dried under high vacuum for 2 hr. The residue was dissolved in 20 ml of methylene chloride, and 0.23 g (14 mol) of tetraethylammonium cyanide was added. After stirring the resulting solution overnight at room temperature, the reaction mixture was concentrated in vacuo. The residue was dissolved in 100 ml of ethyl acetate, and the solution was washed with water and brine. The dried (magnesium sulfate) solution was concentrated in vacuo and the residue was chromatographed over silica with 5% ethyl acetate/hexane. The resulting solid was crystallized from heptane to provide 0.033 g of the title compound as red crystals. m.p. 154°-155° C.

b) 5,11-Dihydro-11-ethyl-6-methoxyimino-2,4-dimethyl-6H-dipyrido[3,2-b:2',3'-e][1,4]diazepine A solution of 5,11-dihydro-11-ethyl-6-methanesulfonyloxy-2,4-dimethyl-6H-dipyrido[3,2-b:2',3'-e]

[1,4]diazepine (0.3 g, 0.75 mmol), methoxylamine hydrochloride (0.15 g, 1.8 mmol) and diisopropylethylamine (0.3 g, 2 mmol) in methylene chloride was stirred at room temperature for 4 days. The organic phase was washed with water, dried, and filtered. The solution was concentrated in vacuo and the residue was chromatographed over silica with 20% ethyl acetate/hexane to give 0.07 g of the title compound, m.p. 164°–166° C.

Example 126

11-Cyclopropyl-5,11-dihydro-4-formyl-6H-dipyrido[3,2-b:2',3'-e][1,4]diazepin-6-one To a solution of oxalyl chloride (0.08 g, 0.6 mmol) in methylene chloride (5 mL) cooled under Argon to −60° C. was added dropwise dimethyl sulfoxide (0.093 g, 1.2 mmol). After 2 minutes 11-cyclopropyl-5,11-dihydro-4-hydroxymethyl-6H-dipyrido[3,2-b:2',3'-e][1,4]diazepin-6-one (0.15 g, 0.53 mmol) in dimethyl sulfoxide/methylene chloride (5 mL) was added dropwise and stirring was continued for an additional 15 minutes. Triethylamine (0.267 g, 2.6 mmol) was added and after 5 minutes the mixture was allowed to warm to room temperature. Water (5 mL) was added and the aqueous phase was separated and extracted with methylene chloride. The combined organic phase was dried and evaporated. Column chromatography over silica gel with 30% ethyl acetate/hexane gave the title compound, which crystallized from ethyl acetate/hexane. Yield 0.045 g, m.p. 220°–222° C.

Example 127

3-Bromo-5,11-dihydro-2-(N,N-dimethylamino)-11-ethyl-4-methyl-6H-dipyrido[3,2-b:2',3'-e][1,4 diazepin-6-one a) 2-Chloro-3-cyano-6-(N,N-dimethylamino)-4-methylpyridine Dimethylamine (8 mL) was added to a solution of 3-cyano-2,6-dichloro-4-methylpyridine (11.6 g) in dioxan (100 mL). After stirring for 2 hours the reaction mixture was diluted with ethyl acetate (1 L), washed with water, dried, filtered, and evaporated to a volume of 20 mL. The crystalline material was filtered to give 5.4 g of the title compound, suitable for use in the next reaction.

b) 5-Bromo-2-chloro-3-cyano-6-(N,N-dimethylamino)-4-methylpyridine

To a suspension of 2-chloro-3-cyano-6-(N,N-dimethylamino)-4-methylpyridine (0.98 g) in acetic acid (10 mL) was added bromine (0.9 g) in acetic acid (1 mL). The reaction mixture was stirred at room temperature for 20 minutes and then warmed to 60° C. for 5 minutes. After cooling to room temperature the mixture was poured into a solution of sodium hydroxide (8 g) in water (100 mL). The mixture was extracted with chloroform (3×30 mL). The combined organic phase was washed, dried, and evaporated to give 1.36 g of the title compound, suitable for use in the next reaction.

c) 5-Bromo-2-chloro-6-(N,N-dimethylamino)-4-methylpyridine-3-carboxamide

A solution of 5-bromo-2-chloro-3-cyano-6-(N,N-dimethylamino)-4-methylpyridine (1.3 g) in concentrated sulfuric acid (3 mL) was heated at 120° C. for 10 minutes. The mixture was cooled, diluted with water (50 mL), and neutralized with saturated sodium carbonate. After extraction with methylene chloride, evaporation of the organic phase gave 1.37 g of the title compound, suitable for use in the next reaction.

d) 3-Amino-5-bromo-2-chloro-6-(N,N-dimethylamino)-4-methylpyridine

Bromine (3.2 g) was added to a solution of sodium hydroxide (2.86 g) in water (30 mL) cooled to 5° C. 5-Bromo-2-chloro-6-(N,N-dimethylamino)-4-methylpyridine-3-carboxamide (4.5 g) was then added, and after 30 minutes the mixture was warmed slowly to 70° C. After 1.5 hours, the mixture was cooled to room temperature and extracted with chloroform. The organic phase was dried and evaporated, and the residue was chromatographed over silica gel with methylene chloride to give 1.8 g of the title compound, suitable for use in the next reaction.

e) 3-Bromo-5,11-dihydro-2-(N,N-dimethylamino)-11-ethyl-4-methyl-6H-dipyrido[3,2-b:2',3'-e][1,4]diazepin-6-one The title compound, m.p. 184°–186° C. was synthesized from 3-amino-5-bromo-2-chloro-6-(N,N-dimethylamino)-4-methylpyridine using procedures analogous to those described above.

Example 128

5,11-Dihydro-11-ethyl-2-(3-hydroxypyrrolidin-1-yl)-4-methyl-6H-dipyrido[3,2-b:2',3'-e][1,4]diazepin-6-one A suspension of the 2-chloro-5,11-dihydro-11-ethyl-4-methyl-6H-dipyrido[3,2-b:2',3'-e][1,4]diazepin-6-one (0.14 g) in 3-hydroxypyrrolidine (0.29 g) in an open test tube was heated at 170° C. for 30 minutes. After cooling to room temperature the mixture was diluted with water and extracted with ethyl acetate. The organic phase was washed, dried, and evaporated. Chromatography over silica gel with ethyl acetate gave the title compound, which crystallized from ethyl acetate. Yield, 0.12 g, m.p. 131°–134° C.

Example 129

5,11-Dihydro-11-ethyl-2-[2-(hydroxyethyl)piperidin-1-yl]-4-methyl-6H-dipyrido[3,2-b:2',3'-e][1,4]diazepin-6-one The title compound, m.p. 234°–237° C., was synthesized from 2-chloro-5,11-dihydro-11-ethyl-4 -methyl-6H-dipyrido[3,2-b:2',3'-e][1,4]diazepin-6-one and 2-(hydroxyethyl)piperidine using procedures analogous to those described above, except that the mixture was heated at reflux for 1.25 hrs, and the product was crystallized from ethyl acetate/ethanol.

Example 130

5,11-Dihydro-11-ethyl-4-methyl-2-(N-methyl-N-[2-(2-pyridinyl)ethyl])amino,6H-dipyrido[3,2-b:2',3'-e][1,4]diazepin-6-one The title compound, m.p. 158°–161° C., was synthesized from 2-chloro-5,11-dihydro-11-ethyl-4-methyl-6H-dipyrido[3,2-b:2',3'-e][1,4]diazepin-6-one and 2-(2-methylaminoethyl)pyridine using procedures analogous to those described above, except that the mixture was heated at 240°–240° C. for 1.25 hrs, and the product was crystallized from ethyl acetate/isopropyl ether.

Example 131

5,11-Dihydro-11-ethyl-2-[3-(hydroxymethyl)piperidin-1-yl]-4-methyl-6H-dipyrido[3,2-b:2',3+-e][1,4]diazepin-6-one The title compound, m.p. 194°–197° C., was synthesized from 2-chloro-5,11-dihydro-11-ethyl-4 -methyl-6H-dipyrido[3,2-b:2',3'-e][1,4]diazepin-6-one and 3- piperidinemethanol using procedures analogous to those described above, except that the mixture was heated at 170°–180° C. for 2.5 hrs, and the product was crystallized from ethyl acetate.

Example 132

5,11-Dihydro-11-ethyl-2-[N-(2-hydroxyethyl)-N-methyl]amino-4-methyl-6H-dipyrido[3,2-b:2',3'-e][1,4diazepin-6-one The title compound, m.p. 139°–142° C., was synthesized from 2-chloro-5,11-dihydro-11-ethyl-4-methyl-6H-dipyrido[3,2-b:2',3'-e][1,4]diazepin-6-one and N-methylethanolamine using procedures analogous to those described above, except that the mixture was heated in a pressure bottle at 170°–180° C. for 5 hrs, and the product was crystallized from ethyl acetate.

Example 133

5,11-Dihydro-11-ethyl-2-[(S)-2-(hydroxymethyl)pyrrolidin-1-yl]-4-methyl-6H-dipyrido[3,2-b:2',3'-e][1,4]diazepin-6-one The title compound, m.p. 238°–240° C., was synthesized from 2-chloro-5,11-dihydro-11-ethyl-4-methyl-6H-dipyrido[3,2-b:2',3'-e][1,4]diazepin-6-one and (S)-(+)-2-pyrrolidinemethanol using procedures analogous to those described above, except that the mixture was heated in a pressure bottle at 170° C. for 3 hrs, and the product was crystallized from chloroform/hexane.

Example 134

5,11-Dihydro-11-ethyl-2-[(R)-2-(hydroxymethyl)pyrrolidin-1-yl]-4-methyl-6H-dibyrido[3,2-b:2',3'-e][1,4]diazepin-6-one The title compound, m.p. 239°–242° C., was synthesized from 2-chloro-5,11-dihydro-11-ethyl-4-methyl-6H-dipyrido[3,2-b:2',3'-e][1,4]diazepin-6-one and (R)-(−)-2-pyrrolidinemethanol using procedures analogous to those described above, except that the mixture was heated in a pressure bottle at 160°–170° C. for 2 hrs, and the product was crystallized from chloroform/hexane.

Example 135

5,11-Dihydro-11-ethyl-2-(2-hydroxyethyl)amino-4-methyl-6H-dipyrido[3,2-b:2',3'-e][1,4diazepin-6-one The title compound, m.p. 241°–244° C., was synthesized from 2-chloro-5,11-dihydro-11-ethyl-4-methyl-6H-dipyrido[3,2-b:2',3'-e][1,4]diazepin-6-one and ethanolamine using procedures analogous to those described above, except that the mixture was heated in a pressure bottle at 260° C. for 50 min., and the product was crystallized from chloroform/ethanol.

Example 136

5,11-Dihydro-11-ethyl-2-(2-imidazolon-1-yl)ethylamino-4-methyl-6H-dipyrido[3,2-b:2',3'-e][1,4]diazepin-6-one The title compound, m.p. >300° C., was synthesized from 2-chloro-5,11-dihydro-11-ethyl-4-methyl-6H-dipyrido[3,2-b:2',3'-e][1,4]diazepin-6-one and 1-(2-aminoethyl)-2-imidazolidone using procedures analogous to those described above, except that the mixture was heated in a pressure bottle at 250° C. for 30 min., and the product was crystallized from acetic acid.

Example 137

5,11-Dihydro-11-ethyl-2-(3-hydroxypropyl)amino-4-methyl-6H-dipyrido[3,2-b:2',3'-e][1,4]diazepin-6-one The title compound, m.p. 222°–224° C., was synthesized from 2-chloro-5,11-dihydro-11-ethyl-4-methyl-6H-dipyrido[3,2-b:2',3'-e][1,4]diazepin-6-one and 3-aminopropanol using procedures analogous to those described above, except that the mixture was heated in a pressure bottle at 210° C. for 40 min., and the product was crystallized from ethyl acetate.

Example 138

11-Cyclopropyl-5,11-dihydro-2-(2,3-dihydroxypropyl)amino-4-methyl-6H-dipyrido[3,2-b:2',3'e][1,4]diazepin-6-one The title compound, m.p. 137°–140° C., was synthesized from 2-chloro-5,11-dihydro-11-ethyl-4-methyl-6H-dipyrido[3,2-b:2',3'-e][1,4]diazepin-6-one and 3-amino-1,2-propanediol using procedures analogous to those described above, except that the mixture was heated in a pressure bottle at 210° C. for 45 min., and the product was crystallized from ethyl acetate/ethanol.

Example 139

2-[N-(2-acetoxyethyl)-N-methyl]amino-5,11-dihydro-11-ethyl-4-methyl-6H-dipyrido[3,2-b:2',3'-e][1,4]diazepin-6-one A mixture of 5,11-dihydro-11-ethyl-2-[N-(2-hydroxyethyl)-N-methyl]amino-4-methyl-6H-dipyrido[3,2-b:2',3'-e][1,4]diazepin-6-one (0.45 g), pyridine (2 mL) and acetic anhydride (0.5 mL) was stirred at room temperature for 3 days. The mixture was evaporated to dryness under reduced pressure, and the residue was chromatographed over silica gel with chloroform to give the title compound which crystallized from diisopropyl ether/methylene chloride, m.p. 145°–147° C.

Example 140

2-(3-Acetoxypyrrolidin-1-yl)-5,11-dihydro-11-ethyl-4-methyl-6H-dipyrido[3,2-b:2',3'-e][1,4diazepin-6-one The title compound, m.p. 188°–189.5° C., was synthesized from 5,11-dihydro-11-ethyl-2-(3-hydroxypyrrolidin-1-yl)-4-methyl-6H-dipyrido[3,2-b:2',3'-e][1,4]diazepin-6-one and acetic anhydride using procedures analogous to those described above. The product was chromatographed over silica gel with ethyl acetate/hexane, and was then crystallized from diisopropyl ether.

Example 141

5,11-Dihydro-11-ethyl-4-methyl-2-(2-oxazolidon-3-yl)-6H-dipyrido[3,2-b:2',3'-e][1,4]diazepin-6-one To a suspension of 5,11-dihydro-11-ethyl-2-(2-hydroxyethyl)amino-4-methyl-6H-dipyrido[3,2b:2',3'-e][1,4]diazepin-6-one (0.25 g) in chloroform (10 mL) was added triphosgene (0.070 g) and diisopropylethylamine (0.2 g). The mixture was heated at reflux for 4 minutes and cooled to room temperature. The mixture was then diluted with ethyl acetate, washed with water, dried, filtered, and evaporated. The residue was chromatographed over silica gel with ethyl acetate/hexane to give the title compound which crystallized from diisopropyl ether/ethyl acetate, m.p. 199°–202° C.

Example 142

5,11-Dihydro-11-ethyl-2-(imidazol-1-yl)-4-methyl-6H-dipyrido[3,2-b:2',3'-e][1,4]diazepin-6-one a) 2-Chloro-3-cyano-6-(imidazol-1-yl)-4-methylpyridine A solution of 2,6-dichloro-3-cyano-4-methylpyridine (5.6 g) and imidazole (2.04 g) in dimethylformamide (10 mL) was heated at 130° C. for 1.25 hours. After cooling to room temperature the mixture was fractionated directly on silica gel with chloroform/ethanol gradient) to give 1.5 g of the title compound, suitable for use in the next reaction.

b) 2-Chloro-6-(imidazol-1-yl)-4-methylpyridine-3-carboxamide

A solution of 2-chloro-3-cyano-6-(imidazol-1-yl)-4-methylpyridine (2.1 g) in concentrated sulfuric acid (5 mL) was heated at 130° C. for 15 minutes. The mixture was cooled to room temperature, diluted with water (10 mL), and adjusted to pH 7 with 20% sodium hydroxide solution followed by solid sodium bicarbonate. The crystalline product was removed by filtration and dried to give 2.35 g of the title compound, suitable for use in the next reaction.

c) 3-Amino-2-chloro-6-(imidazol-1-yl)-4-methylpyridine.

Bromine (2.1 g) was added to a solution of sodium hydroxide (1.8 g) in water (10 mL) cooled on ice, and 2-chloro-6-(imidazol-1-yl)-4-methylpyridine-3-carboxamide (2.3 g) was then added all at once. The mixture was stirred on ice until a clear solution was obtained and was then warmed slowly to 80° C. and maintained at that temperature for 1.5 hours. After cooling to room temperature the crystalline product was removed by filtration and dried to give 0.64 g of the title compound, suitable for use in the next reaction.

d) 5,11-Dihydro-11-ethyl-2-(imidazol-1-yl)-4-methyl-6H-dipyrido[3,2-b:2',3'-e][1,4]diazepin-6-one The title compound, m.p. 243°-245° C., was synthesized from 3-amino-2-chloro-6-(imidazol-1-yl)-4-methylpyridine using procedures analogous to those described above.

Example 143

11-Cyclopropyl-5,11-dihydro-4-phenacyl-6H-dipyrido[3,2-b:2',3'-e][1,4]diazepin-6-one To a solution of 11-cyclopropyl-5,11-dihydro-4-methyl-6H-dipyrido[3,2-b:2',3'-e][1,4]diazepin-6-one (1.0 g) in tetrahydrofuran (25 mL) was added NaH (80% in oil, 0.12 g). The mixture was stirred at room temperature for 30 min. and then cooled to −78° C. Lithium diisopropylamide (1.5M in cyclohexane, 6.6 mL) was added and the mixture was stirred for an additional 45 min. Benzaldehyde (0.53 g) was added, the mixture was stirred at −65° C. for 1 hour and then allowed to warm to room temperature. The reaction was quenched with water and the volatile materials were removed under reduced pressure. The residue was dissolved in ethyl acetate, washed with water, dried, filtered, and evaporated. The residue was chromatographed over silica gel with 40% ethyl acetate/hexane, and then purified by preparative layer chromatography to give 0.1 g of the title compound, m.p. 195°-197° C.,

Example 144

5-Acetyl-2-chloro-11-cyclopropyl-5,11-dihydro-4-methyl-6H-dipyrido[3,2-b:2',3'-e][1,4]diazepin-6-one A mixture of 2-chloro-11-cyclopropyl-5,11-dihydro-4-methyl-6H-dipyrido[3,2-b:2',3'-e][1,4]diazepin-6-one and acetic anhydride with 4-dimethylaminopyridine was heated at 130° C. until a clear solution was obtained. The solvent was evaporated and the residue was chromatographed over silica gel with ethyl acetate/hexane to give 0.85 g of the title compound, which crystallized from isopropyl ether/ethyl acetate, m.p. 204°-206° C.

Example 145

2-Acetamido-5-acetyl-11-cyclopropyl-5,11-dihydro-4-methyl-6H-dipyrido[3,2-b:2',3'-e][1,4]diazepin-6-one A mixture of 2-chloro-11-cyclopropyl-5,11-dihydro-4-methyl-6H-dipyrido[3,2-b:2',3'-e][1,4]diazepin-6-one (5.0 g) and p-methoxybenzylamine (17 mL) in a sealed pressure bottle was heated at 210°-230° C. for 4.5 hours. The mixture was cooled and diluted with ethyl acetate (500 mL) and water (500 mL). The organic phase was separated, washed with 2×200 mL of 10% acetic acid in water, dried, filtered, and evaporated to dryness. The crude product was dissolved in trifluoroacetic acid (25 mL) and heated at 65°-70° C. for 1.5 hours. The volatile material was evaporated and the residue, which was dissolved in ethyl acetate was washed with water and dried. A portion of the residue (2.5 g) in acetic anhydride (10 mL) with 4-dimethylaminopyridine was heated at 130° C. until a clear solution was obtained. The solvent was evaporated and the residue was chromatographed over silica gel with ethyl acetate/hexane to give 0.86 g of the title compound, which crystallized from isopropyl ether/ethyl acetate, m.p. 211°-213° C.

Example 146

2-(N-Acetyl-N-methyl)amino-11-cyclopropyl-5,11-dihydro-4-methyl-6H-dipyrido[3,2-b:2',3'-e][1,4]diazepin-6-one a) To a suspension of 2-acetamido-5-acetyl-11-cyclopropyl-5,11-dihydro-4-methyl-6H-dipyrido[3,2-b:2',3+-e][1,4]diazepin-6-one (0.46 g) in dimethylsulfoxide (10 mL) was added NaH (60% in oil, 0.055 g). The mixture was stirred at room temperature until a clear solution was obtained. Methyl iodide (0.25 g) was added and the mixture was stirred for 30 minutes. Water and ethyl acetate were added and the organic phase was separated, washed, dried, and evaporated. The residue was chromatographed over silica gel with ethyl acetate/hexane to give 5-acetyl-2-(N-acetyl-N-methyl)amino-11-cyclopropyl-5,11-dihydro-4-methyl-6H-dipyrido[3,2-b:2',3'-e][1,4]diazepin-6-one (0.39 g) which crystallized from ethyl acetate, m.p. 222°-224° C.

b) To a solution of 5-acetyl-2-(N-acetyl-N-methyl)amino-11-cyclopropyl-5,11-dihydro-4-methyl-6H-dipyrido[3,2-b:2',3'-e][1,4]diazepin-6-one (0.27 g) in methanol (5 mL) was added hydrazine hydrate (0.070 g). The mixture was left undisturbed for 16 days. The crystalline product was removed by filtration and recrystallized from ethanol/dimethylformamide to give 0.080 g of the title compound, m.p. 268°-270° C.

Example 147

5-Acetyl-2-chloro-5,11-dihydro-11-ethyl-4-methyl-3-nitro-6H-dipyrido[3,2-b:2',3'-e][1,4]diazepin-6-one a) A suspension of 2-chloro-5,11-dihydro-11-ethyl-4-methyl-6H-dipyrido[3,2-b:2',3'-e][1,4]diazepin-6-one (5.1 g) in acetic anhydride (25 mL) was heated at 140° C. for 5 hours. The solvent was evaporated and the residue fractionated over silica gel to give 4.48 g of 5-acetyl-2-chloro-5,11-dihydro-11-ethyl-4-methyl-6H-dipyrido[3,2-b:2',3'-e][1,4]diazepin-6-one, suitable for use in the next reaction.

b) To a solution of 5-acetyl-2-chloro-5,11-dihydro-11-ethyl-4-methyl-6H-dipyrido[3,2-b:2',3'-e][1,4]diazepin-6-one (3.36 g) in acetonitrile (20 mL) cooled on ice was added nitronium tetrafluoroborate (85%, 2.26 g). The mixture was removed from the ice bath and was stirred for 5 hours. The reaction then was quenched with 10% potassium carbonate. Ethyl acetate was added and the organic phase was separated, washed, dried, and evaporated. Chromatography over silica gel gave 0.71 g of the title compound, which crystallized from diisopropyl ether, m.p. 140–141.

Example 148

2-Chloro-5,11-dihydro-11-ethyl-4-methyl-3-nitro-6H-dipyrido[3,2-b:2',3'-e][1,4]diazepin-6-one The title compound was isolated from the chromatographed reaction mixture of Example 147. Crystallization from ethyl acetate/diisopropyl ether gave 0.73 g of the title compound. m.p. 238°–240° C.

Example 149

5,11-Dihydro-11-ethyl-4-methyl-2-methylseleno-3-nitro-6H-dipyrido[3,2-b:2',3'-e][1,4]diazepin-6-one To a mixture of 2-chloro-5,11-dihydro-11-ethyl-4-methyl-3-nitro-6H-dipyrido[3,2-b:2',3'-e][1,4]diazepin-6-one (0.063 g) and dimethyldiselenide (0.11 g) in isopropanol (0.5 mL) in a pressure tube was added sodium borohydride (0.006 g). The tube was sealed and heated at 110° C. for 5 minutes and then left at room temperature for 3 days. The mixture was eluted from a short silica gel column (chloroform) and then fractionated by preparative layer chromatography to give a mixture of 2-chloro-5,11-dihydro-11-ethyl-4-methyl-3-nitro-6H-dipyrido[3,2-b:2',3'-e][1,4]diazepin-6-one and 5,11-dihydro-11-ethyl-4-methyl-2-methylseleno-3-nitro-6H-dypyrido[3,2-b:2', 3'-e][1,4]diazepin-6-one. The mixture was dissolved in dioxan (1 mL) and ethanolamine (0.1 g) was added. The mixture was heated at 100° C. for 2 hours whereupon the remaining starting material had reacted. Evaporation of the solvent and chromatography over silica gel gave the title compound which crystallized on trituration with diisopropyl ether, m.p. 261°–267° C. dec.

Example 150

11-Cyclopropyl-2,3-dichloro-5,11-dihydro-4-methyl-6H-dipyrido[3,2b:2',3'-e][1,4]diazepin-6-one A mixture of 11-cyclopropyl-5,11-dihydro-4-methyl-6H-dipyrido[3,2-b:2',3'-e][1,4]diazepin-6-one (0.5 g) and N-chlorosuccinimide (0.5 g) in carbon tetrachloride (50 mL) was heated under reflux for 6 hours. An additional 0.25 g of N-chlorosuccinimide was added and heating under reflux was continued for 4 hrs more. The mixture was filtered and the solvent was evaporated. The residue was fractionated over silica gel with ethyl acetate/hexane to give the title compound which crystallized from ethyl acetate/ethanol, m.p.>290° C.

The following compounds were prepared in an analogous manner to those described above, or by obvious or known modifications thereof.

Example 151

2-Bromo-11-cyclopropyl-5,11-dihydro-4-methyl-6H-dipyrido[3,2-b:2',3'-e][1,4]diazepin-6-one, m.p. 232°–235° C.

Example 152

8-Amino-5,11-dihydro-2,4-dimethyl-11-ethyl-6H-dipyrido[3,2-b:2',3'-e][1,4]diazepin-6-one, m.p. 204°–205° C.

Example 153

5,11-Dihydro-11-ethyl-4-methyl-2-(thiomorpholin-4-yl)-6H-dipyrido[3,2-b:2',3'-e][1,4]diazepin-6-one, m.p. 221.5°–222.5° C.

Example 154

5,11-Dihydro-11-ethyl-4-methyl-2-(4-methylpiperazin-1-yl)-6H-dipyrido[3,2-b;2',3'-e][1,4]diazepin-6-one hydrochloride, m.p.>200° C.

Example 155

2-Cyano-11-cyclopropyl-5,11-dihydro-4-methyl-6H-dipyrido[3,2-b:2',3'-e][1,4]diazepin-6-one, m.p. 315°–317° C.

Example 156

11-cyclopropyl-5,11-dihydro-2-methoxycarbonyl-4-methyl-6H-dipyrido[3,2-b:2',3'-e][1,4]diazepin-6-one, m.p. 320°–330° C.

Example 157

2,11-Diethyl-5,11-dihydro-4-methyl-6H-dipyrido3,2-b:2',3'-e][1,4]diazepin-6-one, m.p. 188°–190° C.

Example 158

5,11-Dihydro-11-ethyl-2-isopropyl-4-methyl-6H-dipyrido[3,2-b:2',3'-e][1,4]diazepin-6-one, m.p. 212°–214° C.

Example 159

2-tert-Butyl-5,11-dihydro-11-ethyl-4-methyl-6H-dipyrido[3,2-b:2',3'-e][1,4]diazepin-6-one, m.p. 248°–250° C.

Example 160

5,11-Dihydro-11-ethyl-2,3,4-trimethyl-6H-dipyrido[3,2-b:2',3'-e][1,4]diazepin-6-one, m.p. 218°–220° C.

Example 161

5,11-Dihydro-11-ethyl-4-methyl-2-phenethyl-6H-dipyrido[3,2-b:2',3'-e][1,4]diazepin-6-one, m.p. 205°–207° C.

Example 162

5,11-Dihydro-5-methyl-11-phenyl-6H-dipyrido[3,2-b:2',3'-e][1,4]diazepin-6-one, m.p. 75°–80° C.

Example 163

5,11-Dihydro-11-ethyl-4-methyl-2-(3-pyridyl)-6H-dipyrido[3,2-b:2',3'-e][1,4]diazepin-6-one, m.p. 232°–234° C.

Example 164

5,11-Dihydro-11-ethyl-2-hydroxy-4-methyl-6H-dipyrido[3,2-b:2',3'-e][1,4]diazepin-6-one, m.p. 276°–277° C.

Example 165

11-Cyclopropyl-5,11-dihydro-2-iodo-4-methyl-6H-dipyrido[3,2-b:2',3'-e][1,4]diazepin-6-one, m.p. 259°–260° C. (dec.).

Example 166

2-Amino-11-cyclopropyl-5,11-dihydro-4-methyl-6H-dipyrido[3,2-b:2',3'-e][1,4]diazepin-6-one, m.p. 362°–363° C.

Example 167

2-Amino-5,11-dihydro-11-ethyl-4-methyl-6H-dipyrido[3,2-b:2',3'-e][1,4]diazepin-6-one, m.p. 268°–270° C.

Example 168

5,11-Dihydro-2-methoxycarbonyl-11-(3-methoxypropyl)-4-methyl-6H-dipyrido[3,2-b:2',3'-e][1,4]diazepin-6-one, m.p. 150°–155° C.

Example 169

11-Cyclopropyl-5,11-dihydro-2-(4-methoxybenzylamino)-4-methyl-6H-dipyrido[3,2-b:2',3'-e][1,4]diazepin-6-one, m.p. 231°–232° C.

Example 170

11-Cyclopropyl-5,11-dihydro-2-iodo-4-methyl-6H-dipyrido[3,2-b:2',3'-e][1,4diazepin-6-one, m.p. 259°–260° C. (dec.).

Example 171

5,11-Dihydro-11-ethyl-2-iodo-4-methyl-6H-dipyrido[3,2-b:2',3'-e][1,4]diazepin-6-one, m.p. 232°–234° C.

Example A

| Capsules or Tablets | | | |
|---|---|---|---|
| A-1 | | A-2 | |
| Ingredients | Quantity | Ingredients | Quantity |
| Compound of Ex. 2 | 250 mg | Compound of Ex. 2 | 50 mg |
| Starch | 160 mg | Dicalcium Phosphate | 160 mg |
| Microcrys. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 2 is blended into a powder mixture with the premixed excipient materials as identified above with the exception of the lubricant. The lubricant is then blended in and the resulting blend compressed into tablets or filled into hard gelatin capsules.

Example B

| Parenteral Solutions | |
|---|---|
| Ingredients | Quantity |
| Compound of Example 2 | 500 mg |
| Tartaric acid | 1.5 g |
| Benzyl Alcohol | 0.1% by weight |
| Water for injection | q.s. to 100 ml |

The excipient materials are mixed with the water and thereafter the compound of Example 2 is added. Mixing is continued until the solution is clear. The pH of this solution is adjusted to 3.0 and is then filtered into the appropriate vials or ampoules and sterilized by autoclaving.

Example C

| Nasal Solutions | |
|---|---|
| Ingredients | Quantity |
| Compound of Example 2 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 ml |

The excipient materials are mixed with the water and thereafter the compound of Example 2 is added and mixing is continued until the solution is clear. The pH of this solution is adjusted to 4.0 and is then filtered into the appropriate vials or ampoules.

It is claimed:

1. 11-Cyclopropyl-5,11-dihydro-4-methyl-6H-dipyrido[3,2-b:2',3'-e][1,4]diazepin-6-one, or a pharmaceutically acceptable salt thereof.

2. A method for treating HIV-1 infection which comprises administering to a human being infected by HIV-1 a therapeutically effective amount of 11-cyclopropyl-5,11-dihydro-4-methyl-6H-dipyrido[3,2-b:2',3'-e][1,4]diazepin-6-one or a pharmaceutically acceptable salt thereof.

3. A pharmaceutical composition, suitable for treating HIV-1 infection, which comprises a therapeutically effective amount of 11-cyclopropyl-5,11-dihydro-4-methyl-6H-dipyrido[3,2-b:2',3'-e][1,4]diazepin-6-one or a pharmaceutically acceptable salt thereof.

* * * * *